(12) United States Patent
Wang et al.

(10) Patent No.: US 9,802,998 B2
(45) Date of Patent: Oct. 31, 2017

(54) SHORT PEPTIDE-BASED THERAPEUTIC AGENT AND MEDICINAL COMPOSITION INCLUDING THE SAME FOR INHIBITING ACTIVITIES OF CANCER CELLS

(71) Applicant: NATIONAL CHENG KUNG UNIVERSITY, Tainan (TW)

(72) Inventors: Ju-Ming Wang, Tainan (TW); Yu-Wei Hsiao, Chiayi (TW); Jhih-Ying Chi, New Taipei (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 14/841,725

(22) Filed: Sep. 1, 2015

(65) Prior Publication Data
US 2016/0347800 A1 Dec. 1, 2016

(30) Foreign Application Priority Data
May 29, 2015 (TW) .............. 104117476 A

(51) Int. Cl.
| | |
|---|---|
| A61K 38/16 | (2006.01) |
| A61K 38/00 | (2006.01) |
| C07K 5/00 | (2006.01) |
| C07K 7/00 | (2006.01) |
| C07K 16/00 | (2006.01) |
| C07K 17/00 | (2006.01) |
| C07K 14/71 | (2006.01) |
| A61K 38/18 | (2006.01) |
| C07K 14/00 | (2006.01) |

(52) U.S. Cl.
CPC .............. *C07K 14/71* (2013.01); *A61K 38/16* (2013.01); *A61K 38/18* (2013.01); *A61K 38/00* (2013.01); *C07K 14/00* (2013.01)

(58) Field of Classification Search
None
See application file for complete search history.

(56) References Cited

U.S. PATENT DOCUMENTS 8,003,109 B2 * 8/2011 Bottazzi ............. A61K 38/1709
424/185.1
2014/0364374 A1 12/2014 Wang et al.

FOREIGN PATENT DOCUMENTS

CN 104231064 A 12/2014
TW 201446260 A 12/2014

OTHER PUBLICATIONS

UniProt Database, Accession No. P26022, 12 pages (sequence first available May 18, 2010).*
"CEKOL® Carboxymethyl Cellulose," CPKelco, available online at https://www.cpkelco.com/markets-served/pharmaceuticals/products/cekol-carboxymethyl-cellulose-cmc/, 2 pages (accessed on Jan. 8, 2017).*
"Medicinal." Merriam-Webster.com. Merriam-Webster, 14 pages (accessed on Jan. 17, 2017).*
Chun-Pei Cheng, "Characterization of CEBPD elevating PTX3 expression in astrocytes," Theses & Dissertations, Institute of Bioinformatics, National Cheng Kung University, Jul. 22, 2009.
Ju-Ming Wang et al., "CEBPD elevating PTX3 expression participates in the pathogenesis of neurodegeneration," Research Express@NCKU, vol. 18 Issue 8, Jun. 3, 2011.
Chiung-Yuan Ko et al., "CCAAT/enhancer binding protein delta (CEBPD) elevating PTX3 expression inhibits macrophage-mediated phagocytosis of dying neuron cells," Neurobiology of Aging 33(2012) 422.e11-422.e25, 2012.
Yu-Wei Hsiao et al., "CCAAT/Enhancer Binding Protein δ in Macrophages Contributes to Immunosuppression and Inhibits Phagocytosis in Nasopharyngeal Carcinoma," Science Signaling, vol. 6 Issue 284 ra59, Jul. 16, 2013.
Tso-Wen Wang, "Investigation of CEBPD-induced fibrosis in pancreatic stellate cells and consequent effects on pancreatic cancers," Theses & Dissertations, Insitute of Bioinformatics and Biosignal Transduction, National Cheng Kung University, Jul. 29, 2014.
Chiung-Yuan Ko et al., "Biological roles of CCAAT/Enhancer-binding protein delta during inflammation," Journal of Biomedical Science, doi:10.1186/s12929-014-0110-2, Jan. 16, 2015.

* cited by examiner

*Primary Examiner* — Hasan Ahmed
*Assistant Examiner* — Thea D'Ambrosio
(74) *Attorney, Agent, or Firm* — CKC & Partners Co., Ltd.

(57) ABSTRACT

The present invention relates to a short peptide-based therapeutic agent and a medicinal composition including the same for inhibiting activities of cancer cells, which includes at least one short peptide listed as SEQ ID NOs: 1 and 2, either of which is unglycosylated and has no more than 40 amino acid residues, thereby specifically reducing or inhibiting activities of cancer cells such as the cancer cell proliferation, cancer stemness, cell migration, cancer cell invasion, metastasis or drug resistance.

2 Claims, 19 Drawing Sheets
(2 of 19 Drawing Sheet(s) Filed in Color)

SEQUENCE LISTING

```
<160> NUMBER OF SEQ ID NOS: 5

<210> SEQ ID NO 1
<211> LENGTH: 37
<212> TYPE: PRT
<213> ORGANISM: Artificial sequence
<220> FEATURE:
<223> OTHER INFORMATION: The 200th amino acid to 236th amino acid of
      Human sapiens PTX3 (RI37)

<400> SEQUENCE: 1

Arg Pro Met Arg Leu Glu Ser Phe Ser Ala Cys Ile Trp Val Lys Ala
1               5                   10                  15

Thr Asp Val Leu Asn Lys Thr Ile Leu Phe Ser Tyr Gly Thr Lys Arg
            20                  25                  30

Asn Pro Tyr Glu Ile
        35

<210> SEQ ID NO 2
<211> LENGTH: 40
<212> TYPE: PRT
<213> ORGANISM: Artificial sequence
<220> FEATURE:
<223> OTHER INFORMATION: The 320th amino acid to 359th amino acid of
      Human sapiens PTX3 (GI40)

<400> SEQUENCE: 2

Gly Gly Gly Phe Asp Glu Thr Leu Ala Phe Ser Gly Arg Leu Thr Gly
1               5                   10                  15

Phe Asn Ile Trp Asp Ser Val Leu Ser Asn Glu Glu Ile Arg Glu Thr
            20                  25                  30

Gly Gly Ala Glu Ser Cys His Ile
        35                  40

<210> SEQ ID NO 3
<211> LENGTH: 44
<212> TYPE: PRT
<213> ORGANISM: Artificial sequence
<220> FEATURE:
<223> OTHER INFORMATION: The 255th amino acid to 298th amino acid of
      Human sapiens PTX3 (KT44)

<400> SEQUENCE: 3

Lys Leu Val Ala Glu Ala Met Val Ser Leu Gly Arg Trp Thr His Leu
1               5                   10                  15

Cys Gly Thr Trp Asn Ser Glu Glu Gly Leu Thr Ser Leu Trp Val Asn
            20                  25                  30

Gly Glu Leu Ala Ala Thr Thr Val Glu Met Ala Thr
        35                  40

<210> SEQ ID NO 4
<211> LENGTH: 202
<212> TYPE: PRT
<213> ORGANISM: Artificial sequence
```

<220> FEATURE:
<223> OTHER INFORMATION: The 180th amino acid to 381th amino acid of
     Human sapiens PTX3 (pPTX3/C)

<400> SEQUENCE: 4

Glu Thr Ala Ile Leu Phe Pro Met Arg Ser Lys Lys Ile Phe Gly Ser
 1               5                  10                  15

Val His Pro Val Arg Pro Met Arg Leu Glu Ser Phe Ser Ala Cys Ile
                20                  25                  30

Trp Val Lys Ala Thr Asp Val Leu Asn Lys Thr Ile Leu Phe Ser Tyr
            35                  40                  45

Gly Thr Lys Arg Asn Pro Tyr Glu Ile Gln Leu Tyr Leu Ser Tyr Gln
        50                  55                  60

Ser Ile Val Phe Val Val Gly Gly Glu Glu Asn Lys Leu Val Ala Glu
 65                  70                  75                  80

Ala Met Val Ser Leu Gly Arg Trp Thr His Leu Cys Gly Thr Trp Asn
                85                  90                  95

Ser Glu Glu Gly Leu Thr Ser Leu Trp Val Asn Gly Glu Leu Ala Ala
            100                 105                 110

Thr Thr Val Glu Met Ala Thr Gly His Ile Val Pro Glu Gly Gly Ile
        115                 120                 125

Leu Gln Ile Gly Gln Glu Lys Asn Gly Cys Cys Val Gly Gly Gly Phe
    130                 135                 140

Asp Glu Thr Leu Ala Phe Ser Gly Arg Leu Thr Gly Phe Asn Ile Trp
145                 150                 155                 160

Asp Ser Val Leu Ser Asn Glu Glu Ile Arg Glu Thr Gly Gly Ala Glu
                165                 170                 175

Ser Cys His Ile Arg Gly Asn Ile Val Gly Trp Gly Val Thr Glu Ile
            180                 185                 190

Gln Pro His Gly Gly Ala Gln Tyr Val Ser
        195                 200

<210> SEQ ID NO 5
<211> LENGTH: 381
<212> TYPE: PRT
<213> ORGANISM: Artificial sequence
<220> FEATURE:
<223> OTHER INFORMATION: Human sapiens PTX3 (euPTX3)

<400> SEQUENCE: 5

Met His Leu Leu Ala Ile Leu Phe Cys Ala Leu Trp Ser Ala Val Leu
 1               5                  10                  15

Ala Glu Asn Ser Asp Asp Tyr Asp Leu Met Tyr Val Asn Leu Asp Asn
                20                  25                  30

Glu Ile Asp Asn Gly Leu His Pro Thr Glu Asp Pro Thr Pro Cys Ala
            35                  40                  45

Cys Gly Gln Glu His Ser Glu Trp Asp Lys Leu Phe Ile Met Leu Glu
        50                  55                  60

Asn Ser Gln Met Arg Glu Arg Met Leu Leu Gln Ala Thr Asp Asp Val
 65                  70                  75                  80

Leu Arg Gly Glu Leu Gln Arg Leu Arg Glu Glu Leu Gly Arg Leu Ala
                85                  90                  95

Glu Ser Leu Ala Arg Pro Cys Ala Pro Gly Ala Pro Ala Glu Ala Arg
            100                 105                 110

Leu Thr Ser Ala Leu Asp Glu Leu Leu Gln Ala Thr Arg Asp Ala Gly
        115                 120                 125

```
Arg Arg Leu Ala Arg Met Glu Gly Ala Glu Ala Gln Arg Pro Glu Glu
    130                 135                 140
Ala Gly Arg Ala Leu Ala Ala Val Leu Glu Glu Leu Arg Gln Thr Arg
145                 150                 155                 160
Ala Asp Leu His Ala Val Gln Gly Trp Ala Ala Arg Ser Trp Leu Pro
                165                 170                 175
Ala Gly Cys Glu Thr Ala Ile Leu Phe Pro Met Arg Ser Lys Lys Ile
            180                 185                 190
Phe Gly Ser Val His Pro Val Arg Pro Met Arg Leu Glu Ser Phe Ser
        195                 200                 205
Ala Cys Ile Trp Val Lys Ala Thr Asp Val Leu Asn Lys Thr Ile Leu
    210                 215                 220
Phe Ser Tyr Gly Thr Lys Arg Asn Pro Tyr Glu Ile Gln Leu Tyr Leu
225                 230                 235                 240
Ser Tyr Gln Ser Ile Val Phe Val Val Gly Glu Glu Asn Lys Leu
                245                 250                 255
Val Ala Glu Ala Met Val Ser Leu Gly Arg Trp Thr His Leu Cys Gly
            260                 265                 270
Thr Trp Asn Ser Glu Glu Gly Leu Thr Ser Leu Trp Val Asn Gly Glu
        275                 280                 285
Leu Ala Ala Thr Thr Val Glu Met Ala Thr Gly His Ile Val Pro Glu
    290                 295                 300
Gly Gly Ile Leu Gln Ile Gly Gln Glu Lys Asn Gly Cys Cys Val Gly
305                 310                 315                 320
Gly Gly Phe Asp Glu Thr Leu Ala Phe Ser Gly Arg Leu Thr Gly Phe
                325                 330                 335
Asn Ile Trp Asp Ser Val Leu Ser Asn Glu Glu Ile Arg Glu Thr Gly
            340                 345                 350
Gly Ala Glu Ser Cys His Ile Arg Gly Asn Ile Val Gly Trp Gly Val
        355                 360                 365
Thr Glu Ile Gln Pro His Gly Gly Ala Gln Tyr Val Ser
    370                 375                 380
```

SHORT PEPTIDE-BASED THERAPEUTIC AGENT AND MEDICINAL COMPOSITION INCLUDING THE SAME FOR INHIBITING ACTIVITIES OF CANCER CELLS

RELATED APPLICATIONS

This application claims priority to Taiwan Application Serial Number 104117476, filed May 29, 2015, which is herein incorporated by reference.

BACKGROUND

Field of Invention

The present invention relates to a peptide and application thereof. More particularly, the present invention relates to a short peptide-based therapeutic agent, a medicinal composition including the same and a method for inhibiting activities of cancer cells by using the aforementioned medicinal composition.

Description of Related Art

Among the cancer patients suffering from metastatic or malignant tumors that are unlikely eradicated by surgical intervention, the majority of cancer patients receive chemotherapy after surgical intervention of the primary tumor site, for inhibiting the proliferation and metastasis of potential cancel cells. However, even when chemotherapy appears successful, cancer patients still face the risk of recurrence of the same or a drug-resistant cancer. The patients with recurrent cancers, especially the ones with drug-resistant cancers during the chemotherapy, suffer higher risk due to faster metastases occurred in the recurrent cancers.

In the case of carcinomas, it is found that the cancer cells can stimulate the tumor microenvironment to generate various inflammatory factors, white blood cells, overgrown blood vessels, proteases and so on. The cancer-related chronic inflammation also influences the proliferation, metastasis and invasion of cancer cells; however, the causes and the detailed mechanisms of the cancer-related chronic inflammation are still unclear.

In addition to the cancer-related chronic inflammation, in other researches, the tumor microenvironment is also highly related to metastasis and chemoresistance. The tumor microenvironment is constituted of a heterogenous population of stromal cells and other different types of cells, for protecting the tumor, enabling cancer cells to evade and resist the attack of immune cells, thereby conferring drug resistance to the cancer cells.

Besides, based on previous studies of the inventors of the present invention, the decrease of CCAAT/enhancer binding protein delta (CEBPD) of stromal cells contributes to cancer progression. That is to say, the reactivation of CEBPD may be helpful to suppress the cancer cell proliferation.

Fibroblasts and macrophages in the stroma surrounding the tumor are activated by CEBPD and induced to generate secretory factors, including pentraxin-related protein (PTX3). PTX3 has activities of angiogenesis, metastasis and invasion of breast cancer cells, lung cancer cells, and nasopharyngeal cancer cells. In addition, when CEBPD of the cells in the tissue surrounding the tumor is activated, it will facilitate the tumor metastasis and the generation of drug-resistant cancer cells during chemotherapy, all of which has been evidenced by the inventors of the present invention.

There are some commercially available small-molecule anti-cancer drugs, for examples, cis-diammine dichloroplatinum (II) (CDDP; the trade name of Cisplatin), paclitaxel (the trade name of Taxol), 5-Fluorouracil (5-FU) and the like. However, in recent researches, it is found that those commercial small-molecule anti-cancer drugs can activate the CEBPD in fibroblasts and macrophages, resulting in poor cancer treatment such as drug resistance and fast metastasis of cancer cells.

Accordingly, there is an urgent need to develop a small-molecule anti-cancer drug, for overcoming the problems of drug resistance and fast metastasis occurred in conventional small-molecule anti-cancer drugs.

SUMMARY

The invention provides a short peptide-based therapeutic agent, which includes at least one short peptide, and any one of the short peptides has no more than 40 amino acid residues.

Moreover, the invention provides a medicinal composition, which includes a short peptide-based therapeutic agent and a pharmaceutically acceptable carrier, in which the short peptide-based therapeutic agent is an active ingredient, and the short peptide-based therapeutic agent includes at least one short peptide.

Furthermore, the invention provides a method for inhibiting activities of cancer cells by using a medicinal composition, in which the medicinal composition includes a short peptide-based therapeutic agent and a pharmaceutically acceptable carrier, the short peptide-based therapeutic agent is an active ingredient, the short peptide-based therapeutic agent includes at least one short peptide, thereby specifically reducing or inhibiting activities of cancer cells.

According to the aforementioned aspect, the invention provides a short peptide-based therapeutic agent. In an embodiment, the short peptide-based therapeutic agent includes at least one short peptide listed as SEQ ID NOs: 1 and 2, and either of the short peptides is unglycosylated and has no more than 40 amino acid residues for specifically reducing or inhibiting activities of the cancer cells.

According to the another aspect, the invention provides a medicinal composition comprising a short peptide-based therapeutic agent and a pharmaceutically acceptable carrier, in which the short peptide-based therapeutic agent is an active ingredient, the short peptide-based therapeutic agent comprises at least one short peptide listed as SEQ ID NOs: 1 and 2, and either of the short peptides is unglycosylated and has no more than 40 amino acid residues for specifically reducing or inhibiting activities of the cancer cells.

According to the further aspect, the invention provides a method for inhibiting activities of cancer cells by using a medicinal composition, in which the medicinal composition includes a short peptide-based therapeutic agent and a pharmaceutically acceptable carrier, the short peptide-based therapeutic agent is an active ingredient. In an embodiment, the short peptide-based therapeutic agent includes at least one short peptide listed as SEQ ID NOs: 1 and 2, and either of the short peptides is unglycosylated and has no more than 40 amino acid residues, thereby specifically reducing or inhibiting activities of cancer cells in vitro.

According to the aforementioned aspect, the aforementioned medicinal composition can be administrated via a subcutaneous injection, an intratumoral injection, an intravenous injection or an oral administration.

According to the aforementioned aspect, the aforementioned cancer cells can include but be not limited to breast cancer cells, lung cancer cells, nasopharyngeal cancer cells, epithelial cancer cells and any combination thereof.

According to the aforementioned aspect, the aforementioned activities of the cancer cell includes the cancer cell proliferation, cancer stemness, cell migration, cell invasion, metastasis or drug resistance.

With application to the short peptide-based therapeutic agent and medicinal composition including the same for inhibiting activities of cancer cells, the short peptide-based therapeutic agent includes at least one short peptide, and either of the short peptides has no more than 40 amino acid residues, for inhibiting the activity of PTX3, thereby specifically reducing or inhibiting activities of the cancer cell, for example, cancer cell proliferation, cancer stemness, cell migration, cancer cell invasion, metastasis or drug resistance.

It is to be understood that both the foregoing general description and the following detailed description are by examples, and are intended to provide further explanation of the invention as claimed.

BRIEF DESCRIPTION OF THE DRAWINGS

The patent or application file contains at least one drawing executed in color. Copies of this patent or patent application publication with color drawing(s) will be provided by Office upon request and payment of the necessary fee. The disclosure can be more fully understood by reading the following detailed description of the embodiment, with reference made to the accompanying drawings as follows.

DETAILED DESCRIPTION

Figure 1A:
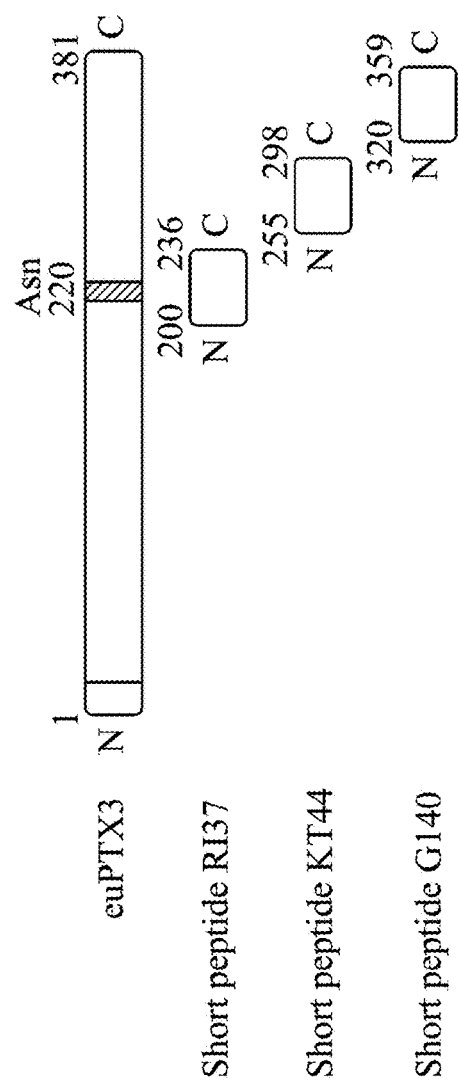
FIG. 1A is a schematic representation of amino acid sequences of various short peptides according to several embodiments of the present invention.

Reference will now be made in detail to the present embodiments of the invention, examples of which are illustrated in the accompanying drawings. Wherever possible, the same reference numbers are used in the drawings and the description to refer to the same or like parts.

As aforementioned, the present invention provides a short peptide-based therapeutic agent, which includes at least one short peptide, and any one of the short peptides is unglycosylated and has no more than 40 amino acid residues, thereby specifically reducing or inhibiting the activity of pentraxin-related protein (PTX3).

Typically, the "short peptide" as discussed hereinafter denotes a short-chain peptide with no more than 40 amino acid residues. In an embodiment, the short peptide-based therapeutic agent includes at least one short peptide listed as SEQ ID NOs: 1 and 2, in which the amino acid sequences of SEQ ID NOs: 1 and 2 are designed according to the human sequence with GenBank Accession No. NP_002843.2, which is herein incorporated by reference. In another embodiment, the short peptide-based therapeutic agent can use two short peptides listed as SEQ ID NOs: 1 and 2. It should be mentioned that, if a peptide had more than 40 amino acid residues (for example, a polypeptide including SEQ ID NOs: 1 and 2), it would be hard to increase the effective dosage of such polypeptide in larger molecular weight, and such peptide would also include ineffective peptide fragments for rendering the subsequent application of the short peptide-based therapeutic agent.

In an embodiment, the short peptides listed as SEQ ID NOs: 1 and 2 can be produced by any conventional method, for example, an artificially synthetic peptide, or a recombinant protein expressed in an expression system using a recombinant gene. The method of making the artificially synthetic peptide or the recombinant protein should be familiar to one skilled in the art rather than being recited repetitively herein.

Typically, the "specifically reducing or inhibiting the binding of PTX3 receptor to PTX3" as discussed hereinafter denotes that the short peptide-based therapeutic agent specifically reduces or inhibits the binding of PTX3 receptor to endogenous PTX3 via consumptive inhibition or competitive inhibition.

In an example, the PTX3 can serve as a soluble stimulator. The short peptide-based therapeutic agent can be a short peptide listed as SEQ ID NOs: 1 or 2. The short peptide-based therapeutic agent can reduce the activity of the endogenous (or full-length) PTX3 by competitive inhibition, or compete binding opportunity of its receptor with the endogenous PTX3, thereby inhibiting the activities of the cancer cells.

In another example, the short peptide-based therapeutic agent can use two short peptides listed as SEQ ID NOs: 1 and 2, for further inhibiting the activities of the cancer cells. It is noted that, the two short peptides listed as SEQ ID NOs: 1 and 2 must be unglycosylated peptide. If the short peptides were pre-glycosylated to have the equal or similar bioactivity as the endogenous PTX3, such glycosylated peptides could not inhibit the activity of the endogenous PTX3 via consumptive inhibition or competitive inhibition.

Typically, the "cancer cells" as discussed hereinafter can include but be not limited to breast cancer cells, lung cancer cells, nasopharyngeal cancer cells, epithelial cancer cells and any combination thereof. The inhibiting "activities" of the cancer cells as discussed hereinafter denotes significant inhibition of cancer cell proliferation, cancer stemness, cell migration, cell invasion, metastasis or drug resistance after the cancer cells are treated by the short peptide-based therapeutic agent of the present invention.

The present invention further provides a medicinal composition comprising a short peptide-based therapeutic agent and a pharmaceutically acceptable carrier, in which the short peptide-based therapeutic agent is an active ingredient as aforementioned.

In application, an effective dosage of the short peptide-based therapeutic agent of the present invention and a pharmaceutically acceptable carrier can be admixed together and administrated to a subject. The "effective dosage" of the short peptide-based therapeutic agent as discussed hereinafter denotes 5 mg/mL to 20 mg/mL thrice weekly. In another example, the effective dosage of the short peptide-based therapeutic agent can be 5 mg/mL to 15 mg/mL thrice weekly. It should be supplemented that, if the effective dosage of the short peptide-based therapeutic agent was less than 5 mg/mL, it could not effectively reduce or inhibit the binding of the PTX3 receptor to PTX3 during a desired duration.

The "pharmaceutically acceptable carrier" as discussed hereinafter refers to an inactive ingredient itself, which can be a carrier, diluent, adjuvant and/or mediator for delivering the active ingredient to a subject; an additive added into the composition for improving the processing or storing properties of the composition; an excipient or other substance for allowing or facilitating the administration at a suitable dose conveniently. The aforementioned pharmaceutically acceptable carrier should not destroy the pharmaceutical activity of the active ingredient, and it is nontoxic when delivering enough therapeutic dose of the active ingredient The suitable "pharmaceutically acceptable carrier", which can be ones well known by one skilled in the manufacturation of the medicinal composition, includes but is not limited to a buffer, diluent, disintegrant, binder, adhesive, humectant, polymer, lubricant, glidant; an additive for masking or neutralizing the unpleasant taste or odor; a dye, fragrance and additive for improving the appearance of the composition. Specific examples of the pharmaceutically acceptable carrier can include but be not limited to citrate buffer, phosphate buffer, acetate buffer, bicarbonate buffer, stearic acid, magnesium stearate, magnesium oxide, sodium and calcium salts of phosphoric and sulfuric acid, magnesium carbonate, talc, gelatin, arabic gum, sodium alginate, pectin, dextrin, mannitol, sorbitol, lactose, sucrose, starch, gelatin, cellulose material (such as cellulose esters of alkanoic acids and cellulose alkyl esters), low melting point wax, cocoa butter, amino acids, urea, alcohols, ascorbic acid, phospholipids, proteins (such as serum albumin), ethylenediaminetetraacetic acid (EDTA), dimethyl sulfoxide (DMSO), sodium chloride or other salts, liposome, glycerol or powder, polymers (such as polyvinyl pyrrolidone, polyvinyl alcohol, and polyethylene glycol) and other pharmaceutically acceptable substances.

In application, the short peptide-based therapeutic agent and the medicinal composition including the same can be administrated via a subcutaneous injection, an intratumoral injection, an intravenous injection or an oral administration, thereby specifically reducing or inhibiting the activity of PTX3 and the activities of the cancer cells. More specifically, as evidenced by the in vitro cell test and in vivo animal experiment, when the short peptide-based therapeutic agent and the medicinal composition including the same is applied on the cancer cell for a desired duration such as 4 weeks to 10 weeks, the activities of the cancer cell, for example, cancer cell proliferation (or also called tumor growth), cancer stemness, cell migration, cell invasion, metastasis (or also called tumor metastasis) or drug resistance, can be inhibited.

Since the short peptide-based therapeutic agent of the present invention including at least one short peptide, either of which has no more than 40 amino acid residues, not only specifically reduces or inhibits the activity of PTX3, but also specifically reduces or inhibits the activities of the cancer cells, for example, cancer cell proliferation (or also called tumor growth), cancer stemness, cell migration, cell invasion, metastasis (or also called tumor metastasis) or drug resistance. Therefore, the short peptide-based therapeutic agent can be applied to the preparation of the medicinal composition for specifically reducing or inhibiting the activity of PTX3.

Thereinafter, various applications of the short peptide-based therapeutic agent and the medicinal composition including the same for inhibiting activities of cancer cells will be described in more details referring to several exemplary embodiments below, while not intended to be limiting. Thus, one skilled in the art can easily ascertain the essential characteristics of the present invention and, without departing from the spirit and scope thereof, can make various changes and modifications of the invention to adapt it to various usages and conditions.

Example 1: Preparation of Short Peptide-Based Therapeutic Agent

Figure 5A:
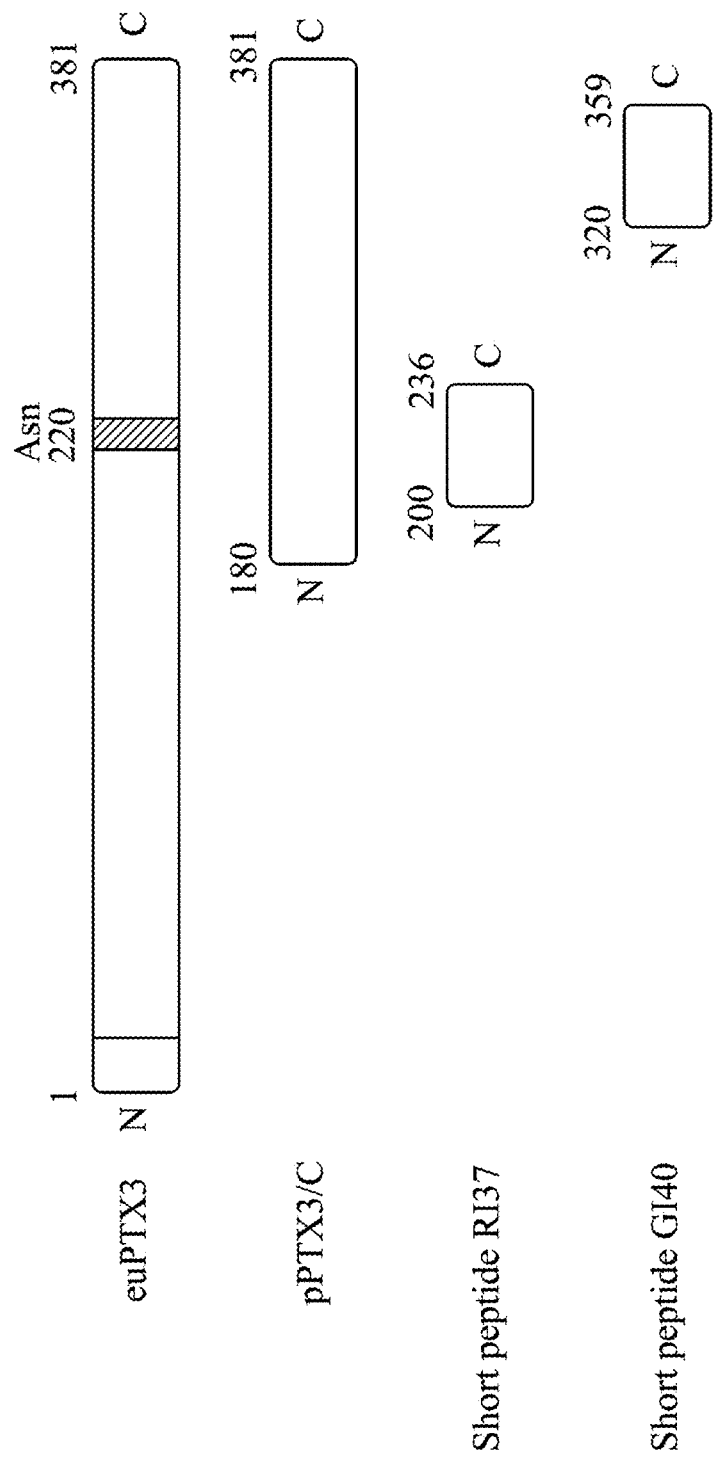
FIG. 5A is a schematic representation of amino acid sequences of various short peptides according to several embodiments of the present invention.

In this example, artificially synthetic peptides of RI37 (having the amino acid sequence listed as SEQ ID NO:1), GI40 (having the amino acid sequence listed as SEQ ID NO:2) and KT44 (having the amino acid sequence listed as SEQ ID NO:3) served as the short peptide-based therapeutic agents, and the recombinant pPTX3/C (having the amino acid sequence listed as SEQ ID NO:4) served as a control group. The designed diagram of short peptides RI37, GI40 and KT44, as well as the recombinant pPTX3, were shown in FIG. 1A. The designed diagram of short peptides RI37 and GI40, as well as the polypeptides euPTX3 and pPTX3/C, were shown in FIG. 5A.

The synthesis of the short peptides RI37, GI40 and KT44 were appointed by Kelowna International Scientific Inc. (Taipei, Taiwan). The polypeptide pPTX3/C was a recombinant protein expressed and purified from prior prokaryotic expression system (*E. coli*). The polypeptide euPTX3 was a commercially available PTX3 product (purchased from R&D system Inc.), which was a recombinant protein purified from mouse myeloma cells (NS0).

Example 2: Established Model of Cell Tests

In this Example, a human breast cancer cell line [MDA-MB231, Deposit Accession Number: BCRC 60425 deposited in Bioresource Collection and Research Center (BCRC), Taiwan of the Food Industry Research and Development Institute, P.O. Box 246, Hsinchu, Taiwan 300, Republic of China, or Deposit Accession Number: ATCC HTB-26; abbreviated hereinafter as MB231] or a CDDP-resistant breast cancer cell line, a human lung cancer cell line A549 (Deposit Accession Number: BCRC 60074 deposited in BCRC; or ATCC CCL-185), a human nasopharyngeal cancer cell line HONE1 (*Int. J. Cancer.* 1990 Jan. 15; 45(1):83-9; *Proc. Natl. Acad. Sci. USA*, Vol. 86, pp. 9524-9528, December 1989) and so on were utilized to evaluate the influence on the inhibition of the cancer cell using the short peptides of Example 1.

The aforementioned cells could be cultured using its respective cell culturing and subculturing method. For example, MDA-MB231 cell, MBR cell, 4T1 cell, 4T1R cell and A549 cell were cultured in Dulbecco's modified Eagle medium (DMEM; Gibco Co.) supplemented with 10% fetal bovine serum (FBS) and antibiotics (containing 50-100 μg/mL of streptomycin and 50-100 U/mL of penicillin). HONE1 cell was cultured in RPMI-1640 medium supplemented with 10% FBS and antibiotics. Those cells were incubated at 37° C. in humidified 5% $CO_2$, the conditions of which were well known by one skilled in the art rather than being recited in detail herein.

Example 3: Evaluation of Influence of Inhibition of Activities of Cancer Cell Using Short Peptide-Based Therapeutic Agent Hereinafter, the cells of Example 2 was added and co-cultured with the short peptide-based therapeutic agents of Example 1, and later evaluated according to the following methods.

1. Evaluation of Influence of Cancer Cell Proliferation Using Short Peptides

After the human breast cancer MB231 cell of Example 2 was co-cultured with the short peptides RI37, GI40 and KT44 of Example 1 for 24 hours or 48 hours, the cell toxicity was analyzed by using MTT [3-(4,5-dimethylthiazol-2-yl)-2,5-diphenol tetrazolium bomide] (Sigma). The transparent and colorless tetrazolium salt of MTT was degraded by mitochondrial dehydrogenase in live cells and converted to blue formazan crystals. Based on the cell viability of the cell in the absence of the short peptides of Example 1 as 100%, the influence of the cancer cell proliferation could be determined by using the short peptides.

Figure 1B:
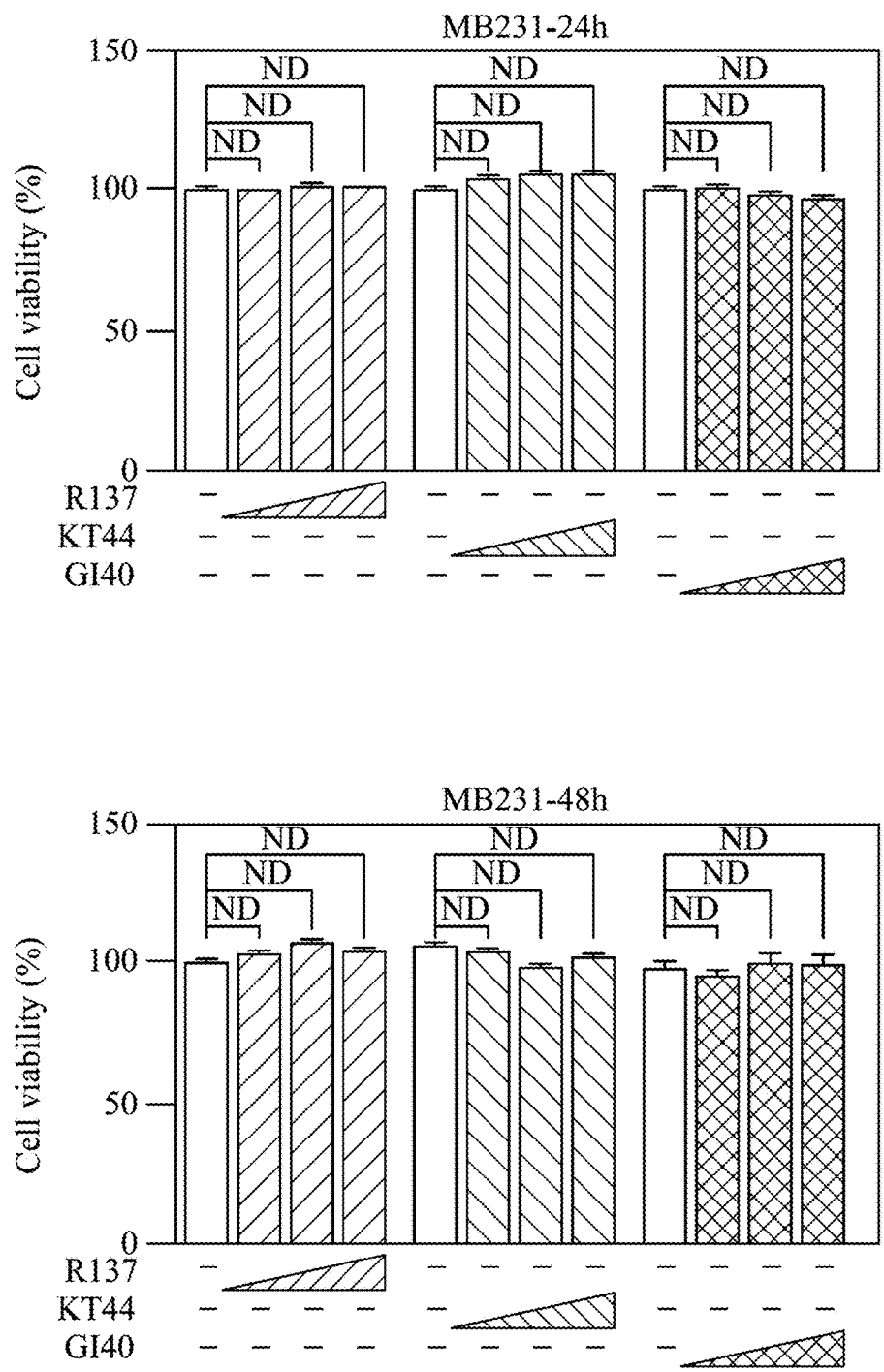
FIG. 1B shows a bar diagram of the cell viability (%) of the breast cancer cell MB231 co-cultured with several short peptides of Example 1 for 24 hours (upper panel) or 48 hours (lower panel) according to several embodiments of the present invention.

Reference was made to FIG. 1B, which showed a bar diagram of the cell viability (%) of the breast cancer MB231 cell co-cultured with several short peptides of Example 1 for 24 hours (upper panel) or 48 hours (lower panel) according to several embodiments of the present invention. In FIG. 1B, the symbol "-" below the horizontal axis referred to the cell cultured in the absence of the specific short peptide, the triangle symbol referred to the cell cultured in an increasing amount of the specific short peptide. According to the result shown in FIG. 1B, the breast cancer MB231 cell co-cultured with the short peptides RI37, GI40 and KT44 of Example 1 for 24 hours or 48 hours had no significant influence on the cell viability.

2. Evaluation of Influence of Cancer Stemness of Cancer Cells Using Short Peptides The breast cancer MB231 cells, the lung cancer A549 cells and the nasopharyngeal cancer HONE1 cells had cancer stemness, and those cancer cells could form spheres co-cultured with the polypeptide euPTX3. Hereinafter, those cancer cells were co-cultured with the short peptides RI37, GI40, KT44 and the polypeptide euPTX3 of Example 1, for evaluating the influence of cancer stemness of the cancer cells using several short peptides of Example 1.

Each well of the multi-well plate with ultra-low attachment surface (Corning Inc.) was inoculated with the cell density $5 \times 10^3$ cells/well of the breast cancer MB231 cell, the lung cancer A549 cell and the nasopharyngeal cancer HONE1 cell, all of which were co-cultured with the short peptides RI37, GI40, KT44 (10 μg/mL or 225 nM of the short peptide) and the polypeptide euPTX3 (2.5 μg/mL) of Example 1 in serum-free medium DMEM/F12 (Gibco) [containing B27 (Invitrogen), 20 ng/mL of epidermal growth factor (EGF; Abcam) and 10 ng/mL of basic Fibroblast Growth Factor (bFGF; Peprotech)]. After 2 weeks of cultivation, the cell spheres were observed by optical microscopy.

Figure 1C:
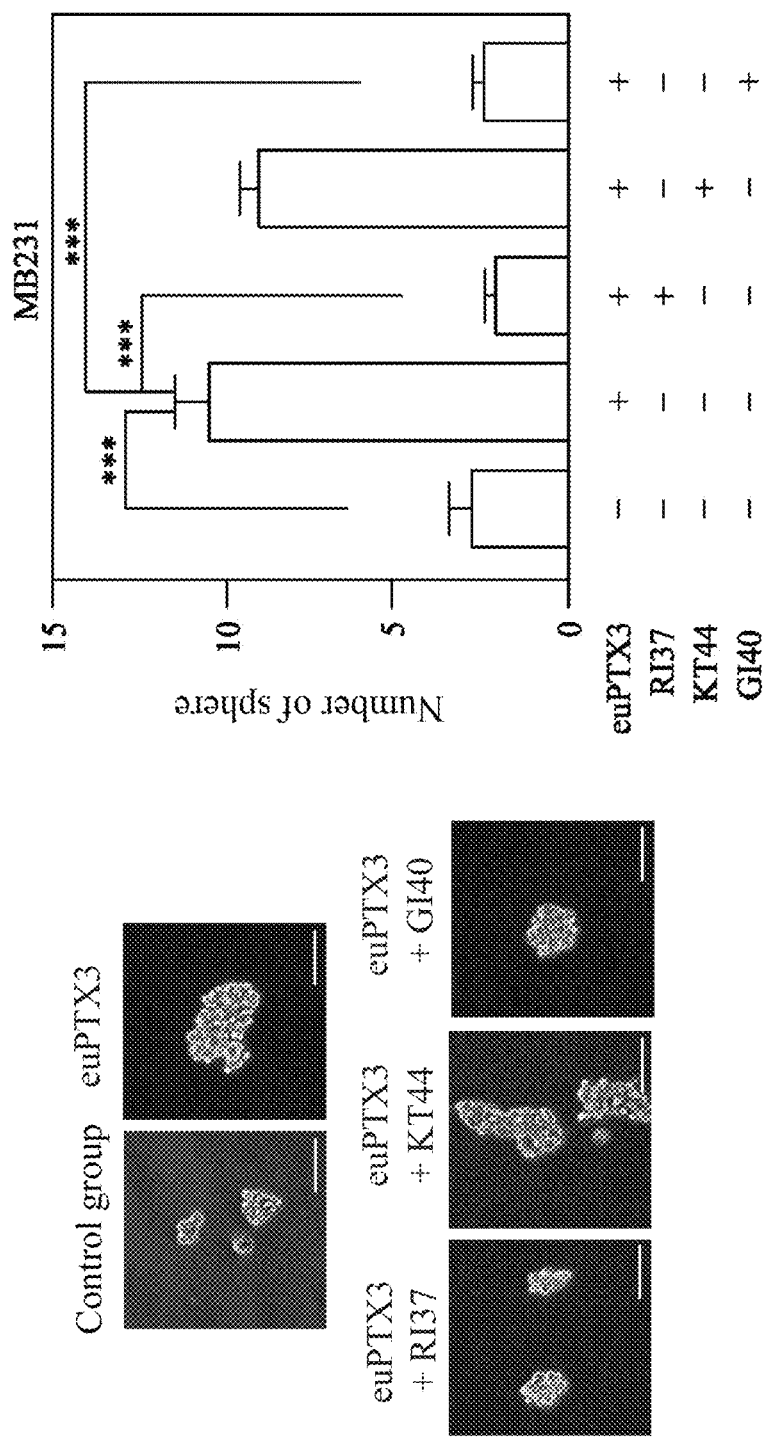
FIG. 1C shows an image (left panel) and a bar diagram of numbers (right panel) of spheres formed by the breast cancer cells MB231 after 2 weeks of co-culture with polypeptide euPTX3 and several short peptides of Example 1 in vitro (at 100-fold magnification).
Figure 2A:
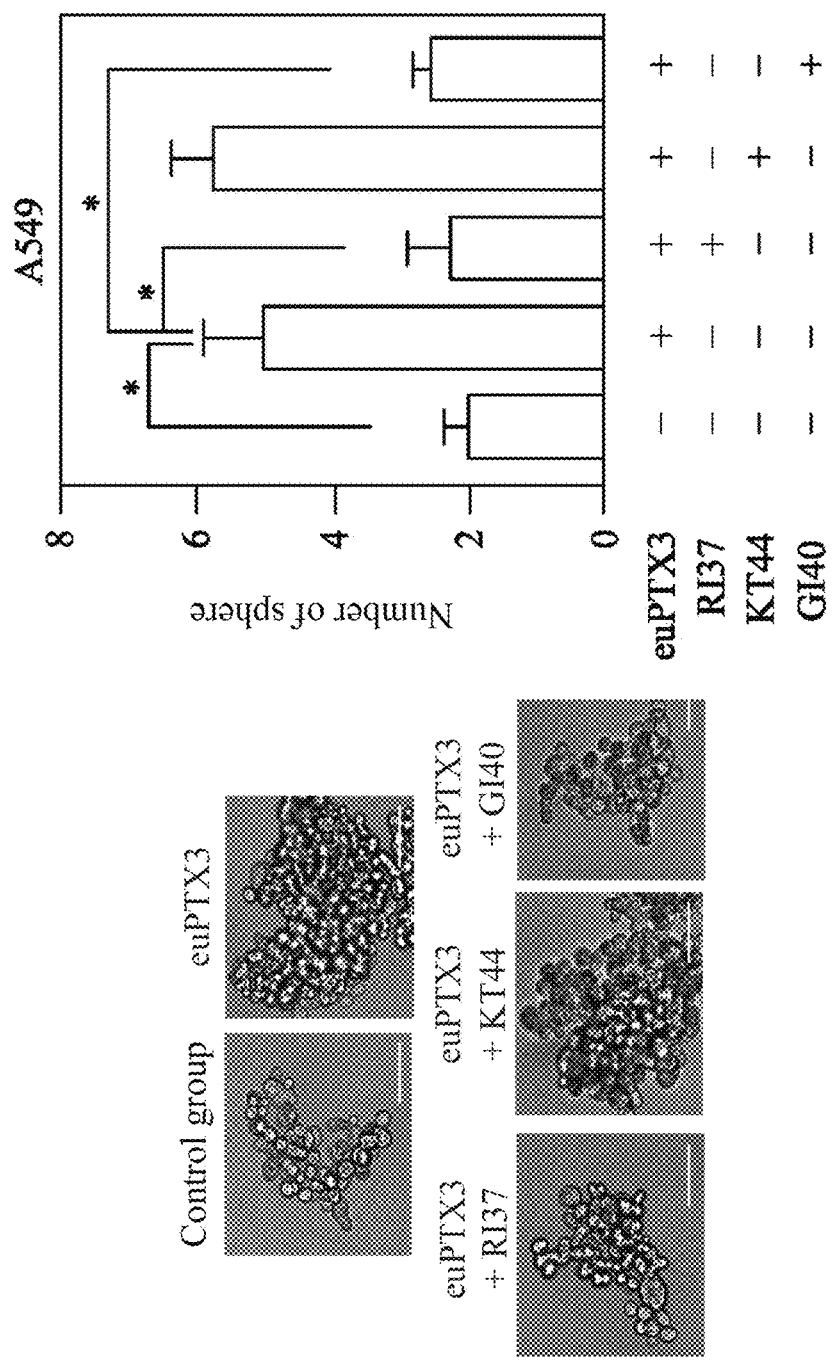
FIG. 2A shows an image (left panel) and a bar diagram of numbers (right panel) of spheres formed by the lung cancer A549 cells after 2 weeks of co-culture with polypeptide euPTX3 and several short peptides of Example 1 in vitro (at 100-fold magnification).
Figure 3A:
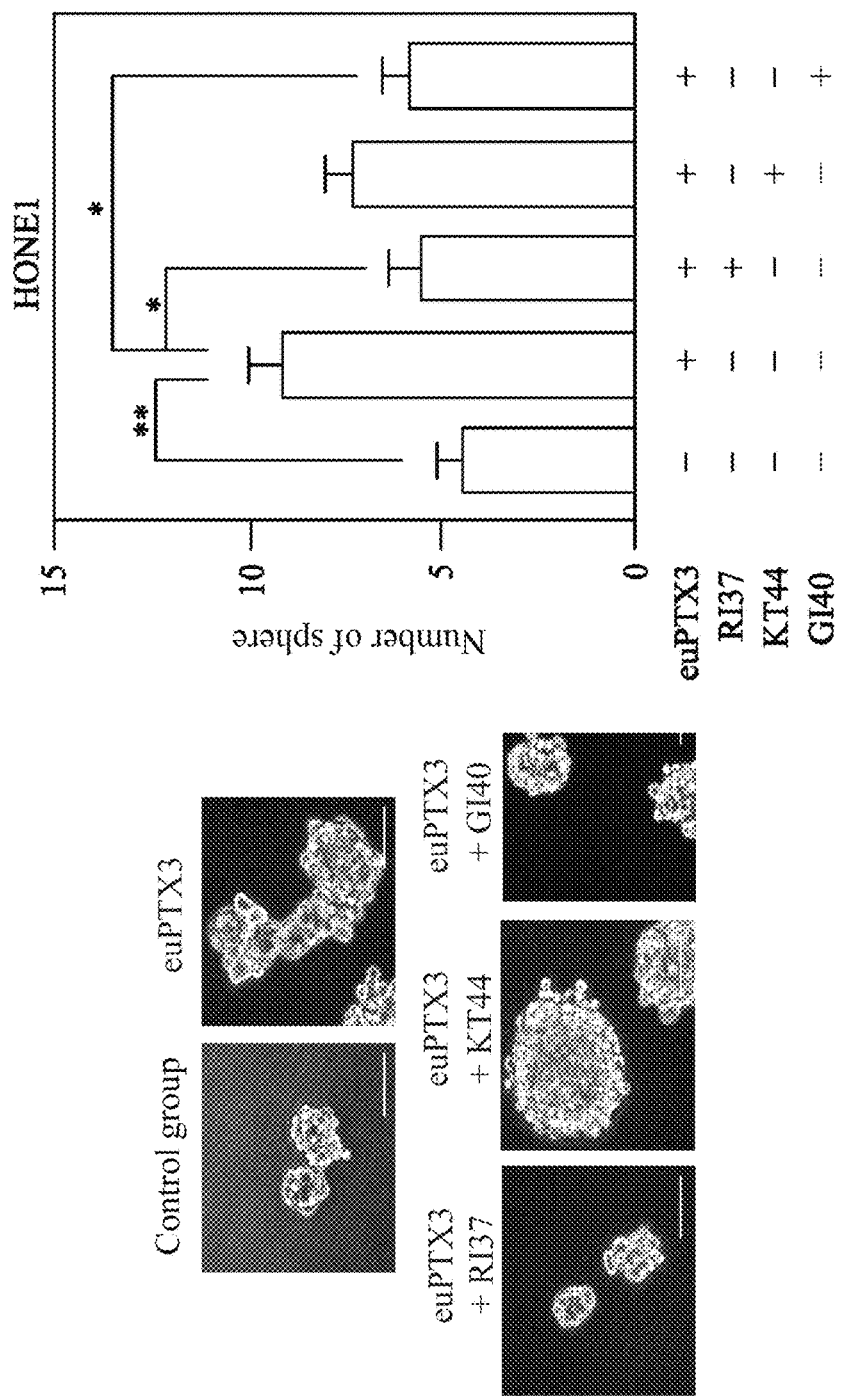
FIG. 3A shows an image (left panel) and a bar diagram of numbers (right panel) of spheres formed by the nasopharyngeal cancer HONE1 cells after 2 weeks of co-culture with polypeptide euPTX3 and several short peptides of Example 1 in vitro (at 100-fold magnification).

Reference was made to FIGS. 1C, 2A and 3A. FIG. 1C showed an image (left panel) and a bar diagram of numbers (right panel) of spheres formed by the breast cancer MB231 cells after 2 weeks of co-culture with several short peptides of Example 1 in vitro. FIG. 2A showed an image (left panel) and a bar diagram of numbers (right panel) of spheres formed by the lung cancer A549 cells after 2 weeks of co-culture with several short peptides of Example 1 in vitro. FIG. 3A showed an image (left panel) and a bar diagram of numbers (right panel) of spheres formed by the nasopharyngeal cancer HONE1 cells after 2 weeks of co-culture with several short peptides of Example 1 in vitro. The images (left panel) of FIGS. 1C, 2A and 3A were taken at 100-fold magnification, and the symbols "-" below the horizontal axis of the bar diagrams (right panel) of FIGS. 1C, 2A and 3A referred to the cells cultured in the absence of the specific short peptide.

According to the result shown in FIGS. 1C, 2A and 3A, in comparison with the cancer cells only co-cultured with the polypeptide euPTX3, the breast cancer MB231 cell, the lung cancer A549 cell and the nasopharyngeal cancer HONE1 cell were co-cultured with the polypeptide euPTX3 and the short peptides RI37 or GI40, the cancer cells co-cultured with the short peptide RI37 or GI40 could effectively inhibit the number of spheres induced by the polypeptide euPTX3, and the differences of numbers had static significance. However, the cancer cells co-cultured with the short peptide KT44 could not inhibit the number of spheres induced by the polypeptide euPTX3.

3. Evaluation of Influence of Drug Resistance of Cancer Cell Using Short Peptides The breast cancer MB231 cell, the lung cancer A549 cell and the nasopharyngeal cancer HONE1 cell had drug resistance, and the drug resistance of those cancer cells could be induced by adding the polypeptide euPTX3. Hereinafter, those cancer cells were co-cultured with the short peptides RI37, GI40, KT44 and the polypeptide euPTX3 of Example 1, for evaluating the influence of drug resistance of the cancer cells using several short peptides of Example 1.

The cell density $1\times10^4$ cells/well of the breast cancer MB231 cell, the lung cancer A549 cell and the nasopharyngeal cancer HONE1 cell were co-cultured with the short peptides RI37, GI40 and KT44 (10 μg/mL or 225 nM of the short peptide) and the polypeptide euPTX3 (2.5 μg/mL) of Example 1. After 1 week of cultivation, those cancer cells were added with 40 μM of CDDP or 100 μM of 5-FU respectively and cultured for 48 hours. Based on the cell viability of the cells only co-cultured with the polypeptide euPTX3 (2.5 μg/mL) as 100%, the influence of drug resistance of the cancer cells of Example 2 using the short peptides of Example 1 could be determined according to the aforementioned MTT assay.

Figure 1D:
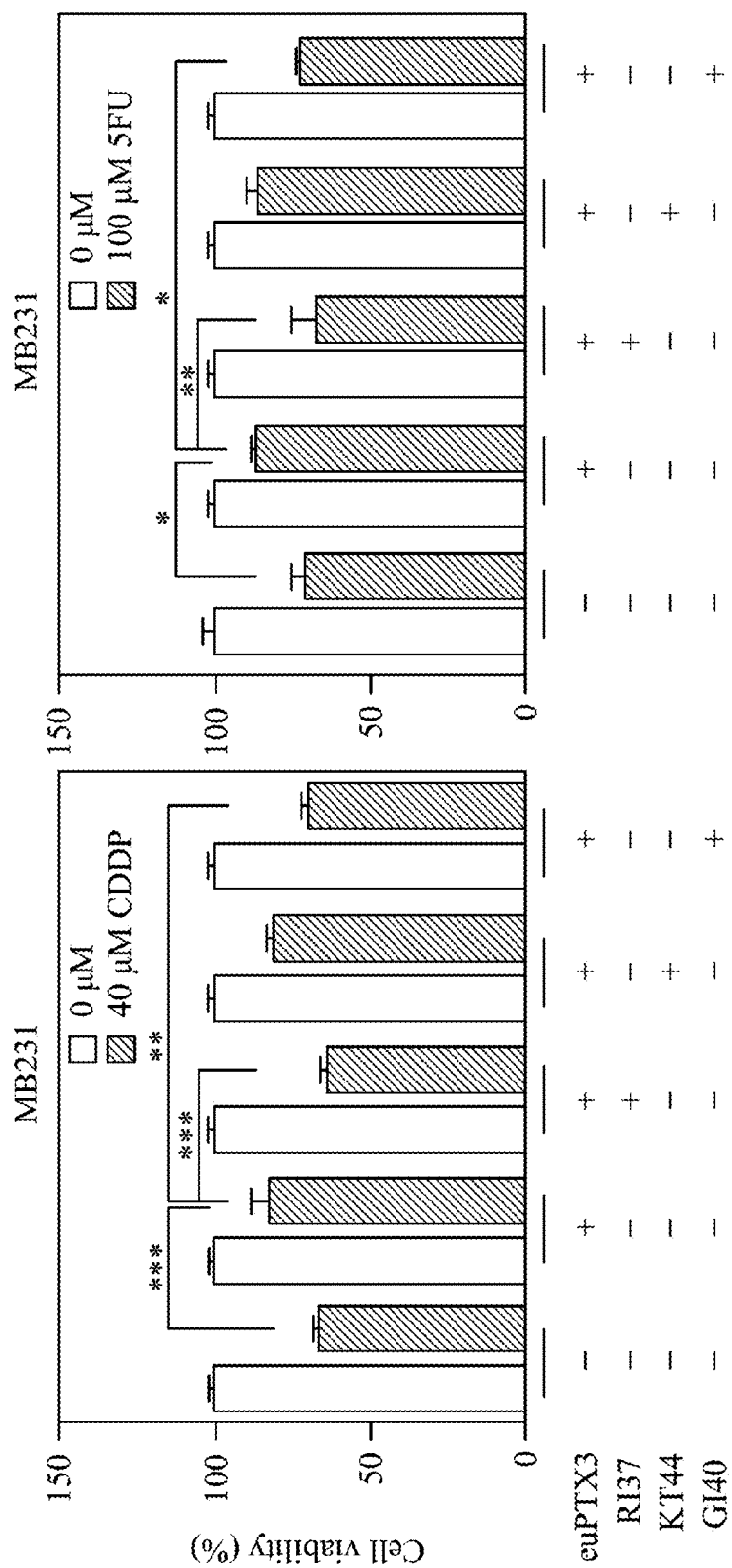
FIG. 1D shows a bar diagram of cell viability (%) of CDDP resistance (left panel) and a bar diagram of cell viability (%) of 5-FU resistance (right panel) of the breast cancer MB231 cells of Example 2 after 1 week of co-cultivation with polypeptide euPTX3 and several short peptides of Example 1 in vitro.
Figure 2B:
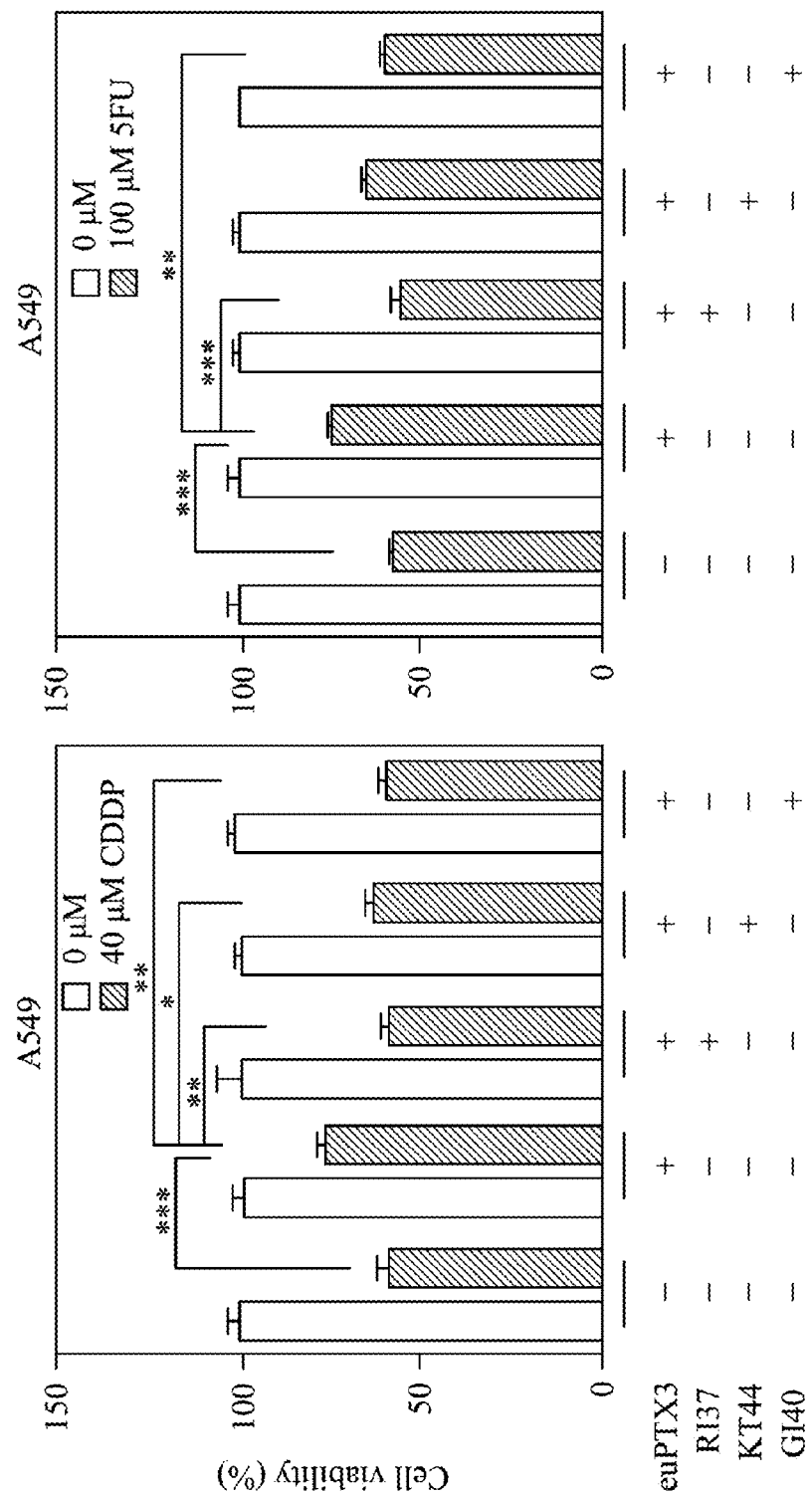
FIG. 2B shows a bar diagram of cell viability (%) of CDDP resistance (left panel) and a bar diagram of cell viability (%) of 5-FU resistance (right panel) of the lung cancer A549 cells of Example 2 after 1 week of co-cultivation with polypeptide euPTX3 and several short peptides of Example 1 in vitro.
Figure 3B:
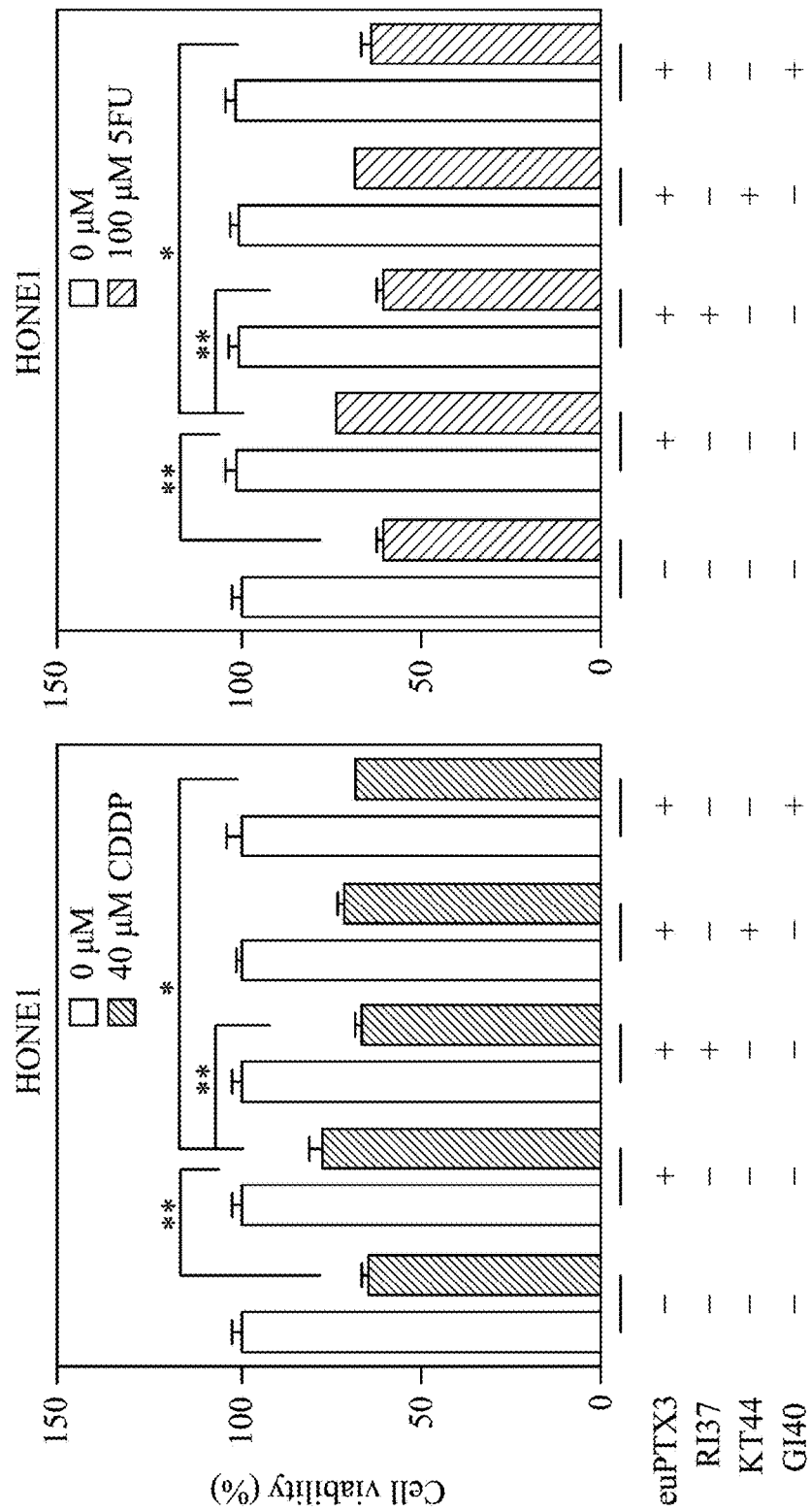
FIG. 3B shows a bar diagram of cell viability (%) of CDDP resistance (left panel) and a bar diagram of cell viability (%) of 5-FU resistance (right panel) of the nasopharyngeal cancer HONE1 cells of Example 2 after 1 week of co-cultivation with polypeptide euPTX3 and several short peptides of Example 1 in vitro.

Reference was made to FIGS. 1D, 2B and 3B. FIG. 1D showed a bar diagram of cell viability (%) of CDDP resistance (left panel) and a bar diagram of cell viability (%) of 5-FU resistance (right panel) of the breast cancer cells MB231 of Example 2 after 1 week of co-cultivation with several short peptides of Example 1 in vitro. FIG. 2B showed a bar diagram of cell viability (%) of CDDP resistance (left panel) and a bar diagram of cell viability (%) of 5-FU resistance (right panel) of the lung cancer cells A549 of Example 2 after 1 week of co-cultivation with several short peptides of Example 1 in vitro. FIG. 3B showed a bar diagram of cell viability (%) of CDDP resistance (left panel) and a bar diagram of cell viability (%) of 5-FU resistance (right panel) of the nasopharyngeal cancer cells HONE1 of Example 2 after 1 week of co-cultivation with several short peptides of Example 1 in vitro. The symbols "-" below the horizontal axis of the bar diagrams (right panel) of FIGS. 1D, 2B and 3B referred to the cells cultured in the absence of the specific short peptide.

According to the results shown in FIGS. 1D, 2B and 3B, in comparison with the cancer cells cultured without the polypeptide euPTX3, the breast cancer MB231 cell, the lung cancer A549 cell and the nasopharyngeal cancer HONE1 cell, which were only co-cultured with the polypeptide euPTX3, could have increase drug resistance to CDDP or 5-FU, and the cell viability of those cancer cells could be also increased.

However, those cancer cells co-cultured with the short peptide RI37 or GI40 could effectively inhibit the drug resistance induced by the polypeptide euPTX3, and the differences of cell viabilities had static significance, in which the short peptide RI37 had stronger inhibitory effect on the drug resistance, followed by the short peptide GI40, but the short peptide KT44 could not significantly inhibit the drug resistance induced by the polypeptide euPTX3.

4. Evaluation of Influence of Migration of Cancer Cell Using Short Peptides

The breast cancer MB231 cell, the lung cancer A549 cell and the nasopharyngeal cancer HONE1 cell could migrate, and cancer cell migration could be promoted by adding the polypeptide euPTX3. Hereinafter, those cancer cells were co-cultured with the short peptides RI37, GI40, KT44 and the polypeptide euPTX3 of Example 1, for evaluating the influence of the cancer cell migration using several short peptides of Example 1.

The cell density $5\times10^4$ cells/well of the breast cancer MB231 cell, the lung cancer A549 cell and the nasopharyngeal cancer HONE1 cell were seeded into each upper insert of 24-well plate (containing 8-μm pore insert per well; BD Biosciences) for 19 hours, and each lower well was added with the short peptides RI37, GI40 and KT44 (10 μg/mL or 225 nM of the short peptide) and the polypeptide euPTX3 (2.5 μg/mL) of Example 1, for evaluating the influence of migration of the cancer cell of Example 2 using several short peptides of Example 1.

The cell density $5\times10^4$ cells/well of the breast cancer MB231 cell, the lung cancer A549 cell and the nasopharyngeal cancer HONE1 cell were seeded into each upper insert of Boyden chamber for 3 hours of cultivation.

And then, the medium in each upper insert was replaced by serum-free medium, and the medium in each lower well was added with the short peptides RI37, GI40, KT44 and the polypeptide euPTX3 of Example 1. The cells inside each upper insert were wiped with cotton swabs and removed after 16 hours of cultivation. Remaining cells that had migrated to the bottom of the insert membrane were stained by 4',6-diamidino-2-phenylindole (DAPI; Invitrogen) and calculated under fluorescence microscopy with 200-fold magnification.

Figure 1E:
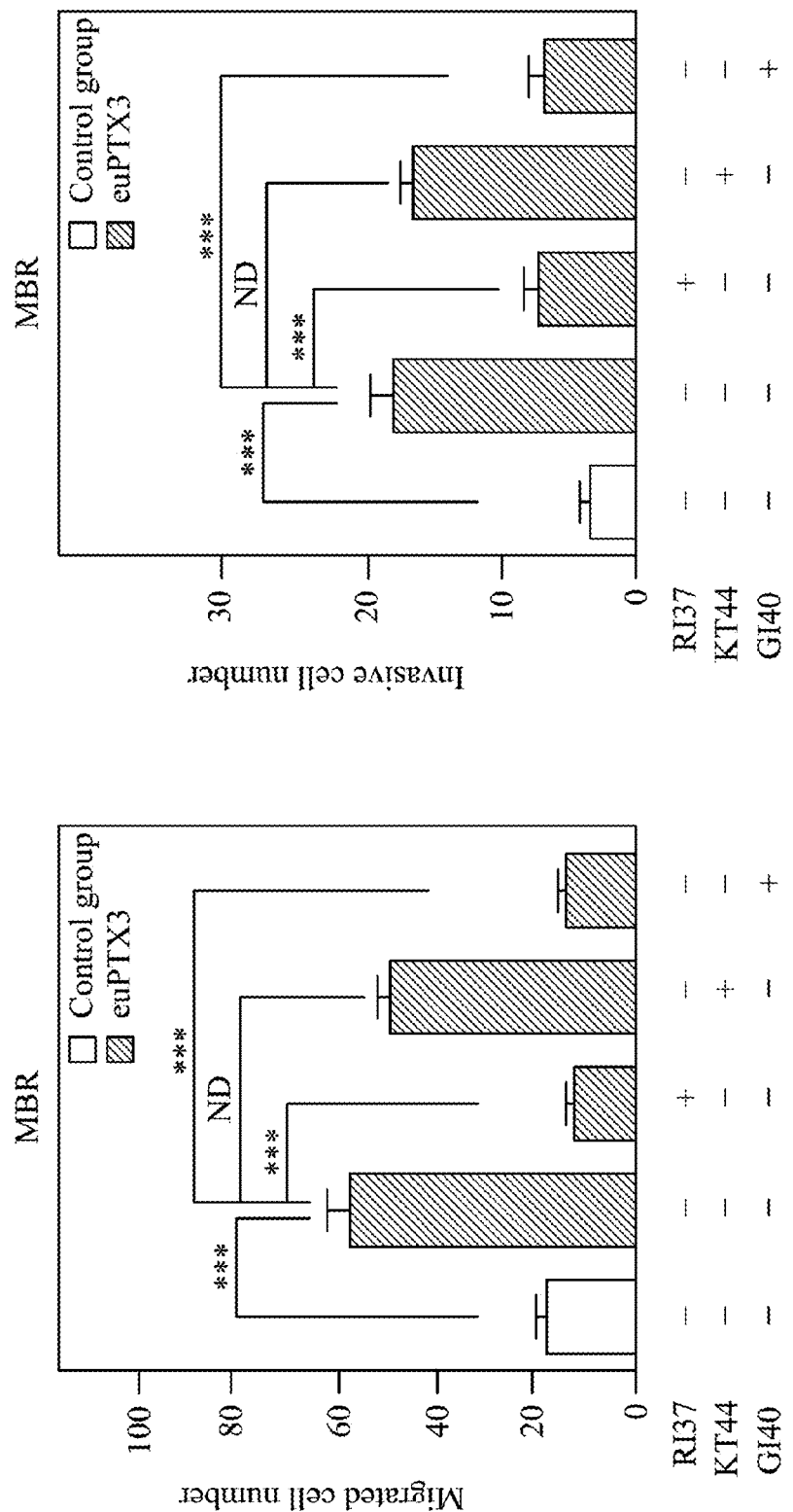
FIG. 1E shows a bar diagram of migrated cell numbers (left panel) or invasive cell number (right panel) of the drug-resistant breast cancer MB231R (MBR) cells of Example 2 after co-cultivation with polypeptide euPTX3 and several short peptides of Example 1 in vitro.
Figure 2C:
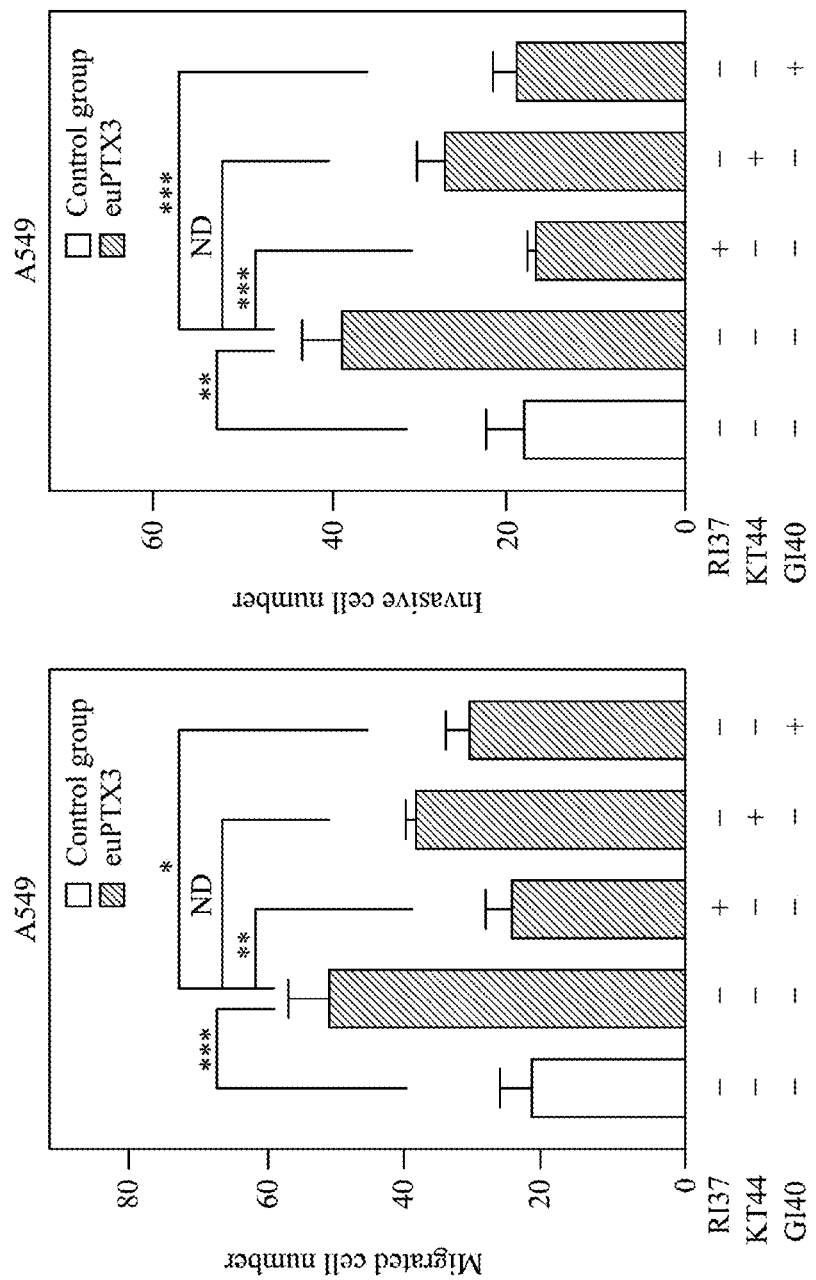
FIG. 2C shows bar diagrams of migrated cell numbers (left panel) and invasive cell numbers (right panel) of the lung cancer A549 cells of Example 2 after 1 week of co-cultivation with polypeptide euPTX3 and several short peptides of Example 1 in vitro.
Figure 3C:
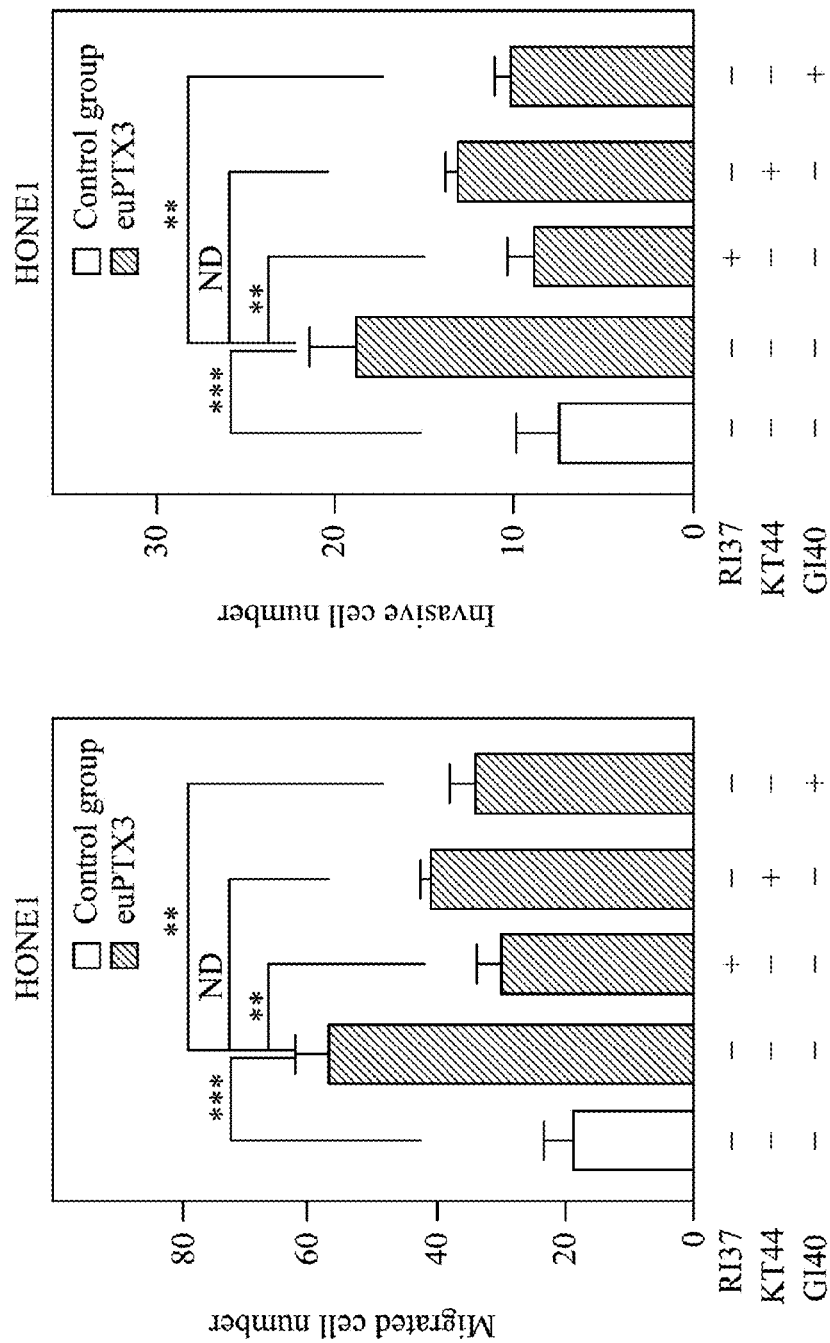
FIG. 3C shows bar diagrams of migrated cell numbers (left panel) and invasive cell numbers (right panel) of the nasopharyngeal cancer HONE1 cells of Example 2 after 1 week of co-cultivation with polypeptide euPTX3 and several short peptides of Example 1 in vitro.

Reference was made to FIG. 1E (left panel), 2C (left panel), 3C (left panel) and 5B (left panel). The left panel of FIG. 1E was depicted to a bar diagram of migrated cell numbers of the drug-resistant breast cancer MB231R (MBR) cells of Example 2 after 1 week of co-cultivation with several short peptides of Example 1 in vitro. The left panel of FIG. 2C was depicted to a bar diagram of migrated cell numbers of the lung cancer A549 cells of Example 2 after 1 week of co-cultivation with several short peptides of Example 1 in vitro. The left panel of FIG. 3C was depicted to a bar diagram of migrated cell numbers of the nasopharyngeal cancer HONE1 cells of Example 2 after 1 week of co-cultivation with several short peptides of Example 1 in vitro. In the left panels of FIG. 1E, FIG. 2C and FIG. 3C, the concentration of the polypeptide euPTX3 was 2.5 μg/mL, and the concentration of the short peptides RI37, GI40, KT44 was 10 μg/mL.

Figure 5B:
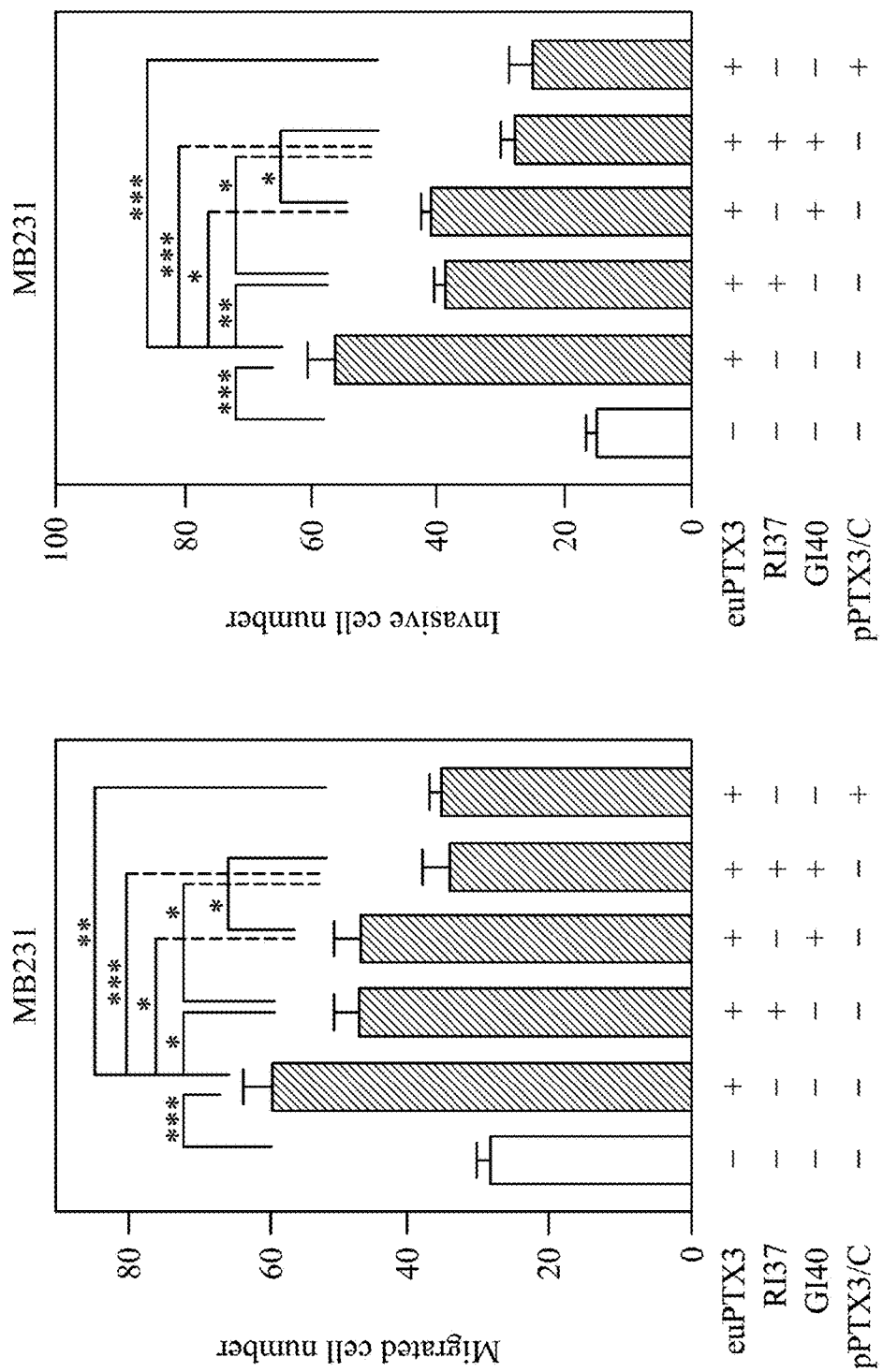
FIG. 5B shows bar diagrams of migrated cell numbers (left panel) and invasive cell numbers (right panel) of the breast cancer MB231R (MBR) cells of Example 2 induced by the polypeptide euPTX3 that can be inhibited in vitro by several short peptides and the polypeptide euPTX3 according to several embodiments of the present invention.

The left panel of FIG. 5B was depicted to a bar diagram of migrated cell numbers of the breast cancer MB231R (MBR) cells of Example 2 after co-cultivation with several short peptides of Example 1 in vitro. In the left panel of FIG. 5B, the concentration of the polypeptide euPTX3 was 2.5 μg/mL, the concentration of the short peptide RI37 was 3.7 μg/mL, the concentration of the short peptide GI40 was 4 μg/mL, and the concentration of the pPTX3/C was 10 μg/mL, so that the polypeptide euPTX3, the short peptide RI37, the short peptide GI40, the pPTX3/C had the identical molecular number. The symbols "-" below the horizontal axis of the bar diagrams (left panels) of FIGS. 1E, 2C, 3C and 5B referred to the cells cultured in the absence of the specific short peptide.

According to the results shown in left panels of FIGS. 1E, 2C, 3C and 5B, in comparison with the cancer cells only cultured with the polypeptide euPTX3, the breast cancer MB231 cell, the lung cancer A549 cell and the nasopharyngeal cancer HONE1 cell, which were only co-cultured with the polypeptide euPTX3, could have increase migrated cell numbers. However, those cancer cells co-cultured with the short peptide RI37 or GI40 could effectively inhibit the migrated cell numbers induced by the polypeptide euPTX3, and the differences of migrated cell numbers had static significance, but the short peptide KT44 could not inhibit the migrated cell numbers induced by the polypeptide euPTX3.

It should be supplemented that, the left panel of FIG. 5B further evidenced that the combination with the short peptides RI37 and GI40 could provide better inhibition effect of migrated cell numbers induced by the polypeptide euPTX3. Although the pPTX3/C can inhibit migrated cell numbers induced by the polypeptide euPTX3, the polypeptide euPTX3, which had larger molecule including the fragments of the short peptides RI37, KT44 and GI40, would render the subsequent application to the short peptide-based therapeutic agent, and it would difficult to increase its effective dosage due to its larger molecular weight. Moreover, pPTX3/C produced by $E.\ coli$ had no activating group for glycosylation introduced into pPTX3/C produced by $E.\ coli$; however, the recombinant protein produced by $E.\ coli$ was easily contaminated by endotoxin (LPS), so that it would be higher risk of such recombinant protein for directly treating human. Therefore, the short peptides RI37, KT44 and GI40 synthesized artificially and chemically had advantage of their smaller molecular weight and solution of problems of endotoxin contamination.

5. Evaluation of Influence of Invasion of Cancer Cell Using Short Peptides

The breast cancer MB231 cell, the lung cancer A549 cell and the nasopharyngeal cancer HONE1 cell could invade, and cancer cell invasion could be promoted by adding the polypeptide euPTX3. Hereinafter, those cancer cells were co-cultured with the short peptides RI37, GI40, KT44 and the polypeptide euPTX3 of Example 1, for evaluating the influence of the cancer cell invasion using several short peptides of Example 1.

The cell density $5\times10^4$ cells/well of the breast cancer MB231 cell, the lung cancer A549 cell and the nasopharyngeal cancer HONE1 cell were seeded into each upper insert of 24-well plate (containing 8-μm pore insert per well; BD Biosciences), the upper insert and the lower well were separated by the polyethelene terephthalate membrane coated with matrigel (purchased from BD Bioscience), and cultured for 3 hours.

Next, the medium in each upper insert was replaced by serum-free medium, and the medium in each lower well was added with the short peptides RI37, GI40, KT44 and the polypeptide euPTX3 and pPTX3/C of Example 1. The cells inside each upper insert were wiped with cotton swabs and removed after 16 hours of cultivation. Remaining cells that had migrated to the bottom of the insert membrane were stained by 4',6-diamidino-2-phenylindole (DAPI; Invitrogen) and calculated under fluorescence microscopy with 200-fold magnification.

Reference was made to FIG. 1E (right panel), 2C (right panel), 3C (right panel) and 5B (right panel). The right panel of FIG. 1E was depicted to a bar diagram of invasive cell numbers of the drug-resistant breast cancer MB231R (MBR) cells of Example 2 after co-cultivation with several short peptides of Example 1 in vitro. The right panel of FIG. 2C was depicted to a bar diagram of invasive cell numbers of the lung cancer A549 cells of Example 2 after co-cultivation with several short peptides of Example 1 in vitro. The right panel of FIG. 3C was depicted to a bar diagram of invasive cell numbers of the nasopharyngeal cancer HONE1 cells of Example 2 after co-cultivation with several short peptides of Example 1 in vitro. In the right panel of FIG. 1E, the right panel of FIG. 2C and the right panel of FIG. 3C, the concentration of the polypeptide euPTX3 was 2.5 μg/mL, and the concentration of the short peptides RI37, GI40, KT44 was 10 μg/mL.

The right panel of FIG. 5B was depicted to a bar diagram of invasive cell numbers of the breast cancer MB231R (MBR) cells of Example 2 after co-cultivation with several short peptides of Example 1 in vitro. In the right panel of FIG. 5B, the concentration of the polypeptide euPTX3 was 2.5 μg/mL, the concentration of the short peptide RI37 was 3.7 μg/mL, the concentration of the short peptide GI40 was 4 μg/mL, and the concentration of the pPTX3/C was 10 μg/mL, so that the polypeptide euPTX3, the short peptide RI37, the short peptide GI40, the pPTX3/C had the identical molecular number. The symbols "-" below the horizontal axis of the bar diagrams (right panels) of FIGS. 1E, 2C, 3C and 5B referred to the cells cultured in the absence of the specific short peptide.

According to the results shown in right panels of FIGS. 1E, 2C, 3C and 5B, in comparison with the cancer cells only cultured with the polypeptide euPTX3, the breast cancer MB231 cell, the lung cancer A549 cell and the nasopharyngeal cancer HONE1 cell, which were only co-cultured with the polypeptide euPTX3, could have increase invasive cell numbers. However, those cancer cells co-cultured with the short peptide RI37 or GI40 could effectively inhibit the invasive cell numbers induced by the polypeptide euPTX3, and the differences of invasive cell numbers had static significance, but the short peptide KT44 could not inhibit the invasive cell numbers induced by the polypeptide euPTX3.

It should be supplemented that, the right panel of FIG. 5B further evidenced that the combination with the short peptides RI37 and GI40 could provide better inhibition effect of invasive cell numbers induced by the polypeptide euPTX3 in comparison to the only use of the short peptides RI37 or GI40. Although the pPTX3/C can inhibit invasive cell numbers induced by the polypeptide euPTX3, the polypeptide euPTX3, which had larger molecule including the fragments of the short peptides RI37, KT44 and GI40, would render the subsequent application to the short peptide-based therapeutic agent, and it would difficult to increase its effective dosage due to its larger molecular weight. Moreover, pPTX3/C produced by $E.\ coli$ had no activating group for glycosylation introduced into pPTX3/C produced by $E.\ coli$; however, the recombinant protein produced by $E.\ coli$ was easily contaminated by endotoxin (LPS), so that it would be higher risk of such recombinant protein for directly treating human. Therefore, the short peptides RI37, KT44 and GI40 synthesized artificially and chemically had advantage of their smaller molecular weight and solution of problems of endotoxin contamination.

Example 4: Evaluation of the Influence of Tumor Using Short Peptides in Animal Experiment Model 1. Establishment of Animal Experiment Model In this Example, $1\times10^6$ mCherry fluorescent protein-labeled CDDP-resistant mouse 4T1 cells (4T1R; ATCC CRL-2539) were inoculated subcutaneously to the rear side of the back of six to eight-week-old female BALB/c mice (purchased from Laboratory Animal Center of National Cheng Kung University). After 1 week of inoculation, the mice were intraperitoneally injected with 5 mg/kg of CDDP [dissolved in 1% (w/v) DMSO] or only 1% (w/v) of DMSO once weekly, and intratumorally uninjected or injected with 50 μg of the short peptides RI37, GI40 and KT44 of Example 1 twice weekly. The mice were sacrificed after six weeks of inoculation. Spleen, kidneys, lungs and liver were obtained, tumor weight of those organs were measured according to 6 replications per group, and the metastatic activity and the number of metastatic nodules per organ were confirmed by IVIS Spectrum Imaging System 200 (Caliper). The tumor size was measured by a commercial external caliper, and the tumor volume (V) was calculated by the following formula (I):

$$V=(w \times l^2) \times 0.52 \qquad (I)$$

In the formula (I), w was referred to tumor width, l was referred to tumor length. Each condition of the experiment was repeated at least thrice.

Besides, $1 \times 10^6$ mCherry fluorescent protein-labeled CDDP-resistant human MDA-MB-231 cells (MB231R; ATCC CRL-2539) were inoculated subcutaneously to the rear side of the back of six to eight-week-old female NOD-SCID immunodeficiency mice (purchased from Laboratory Animal Center of National Cheng Kung University). After 1 week of inoculation, the mice were intraperitoneally injected with 5 mg/kg of CDDP [dissolved in 1% (w/v) DMSO] or only 1% (w/v) of DMSO once weekly, and intratumorally uninjected or injected with 50 μg of the short peptides RI37, GI40 and KT44 of Example 1 twice weekly. The mice were sacrificed after ten weeks of inoculation. Spleen, kidneys, lungs and liver were obtained, tumor weight of those organs were measured according to 3 replications per group, and the metastatic activity and the number of metastatic nodules per organ were confirmed by IVIS Spectrum Imaging System. The tumor size was measured by a commercial external caliper, and the tumor volume (V) was calculated by the following formula (I). Each condition of the experiment was repeated at least thrice.

2. Evaluation of Influence of Allograft Tumor Using Short Peptides

Figure 4A:
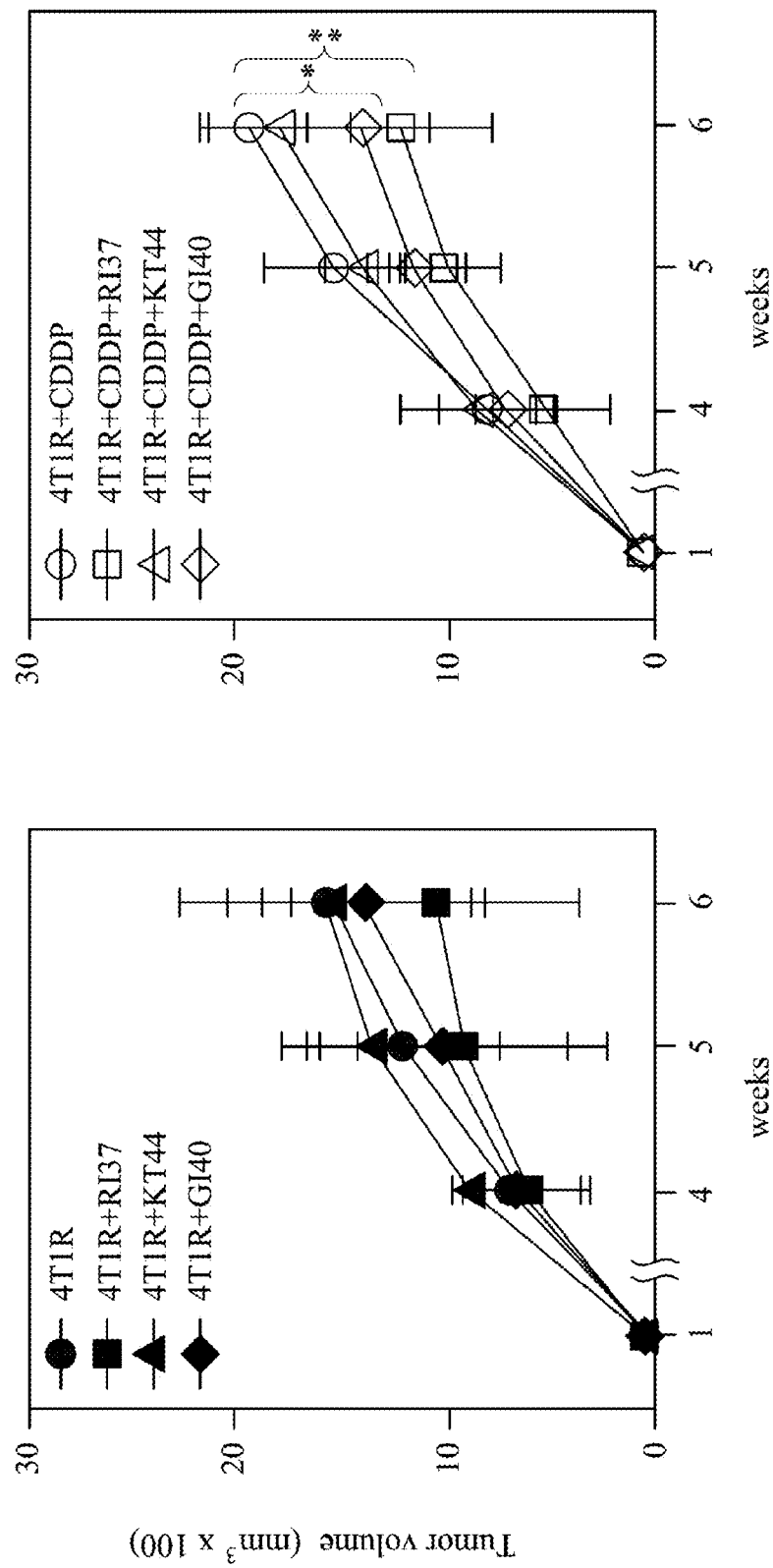
FIG. 4A shows curve diagrams of tumor size of drug-resistant 4T1R breast cancer inhibited by several short peptides of Example 1 (left panel) or inhibited by combination with several short peptides of Example 1 and CDDP (right panel) in vivo.

Reference was made to FIG. 4A, which showed curve diagrams of tumor size of drug-resistant 4T1R breast cancer inhibited by several short peptides of Example 1 (left panel) or inhibited by combination with several short peptides of Example 1 and CDDP (right panel) in vivo. According to the results shown in FIG. 4A, the short peptides RI37 and GI40 of Example 1 could inhibit tumor growth, reduce the drug resistance generated by the tumor from drug-resistant 4T1R breast cancer cell, in which the short peptide RI37 had stronger inhibitory effect on the tumor growth, followed by the short peptide GI40, but the short peptide KT44 could not significantly inhibit the tumor growth.

Figure 4B:
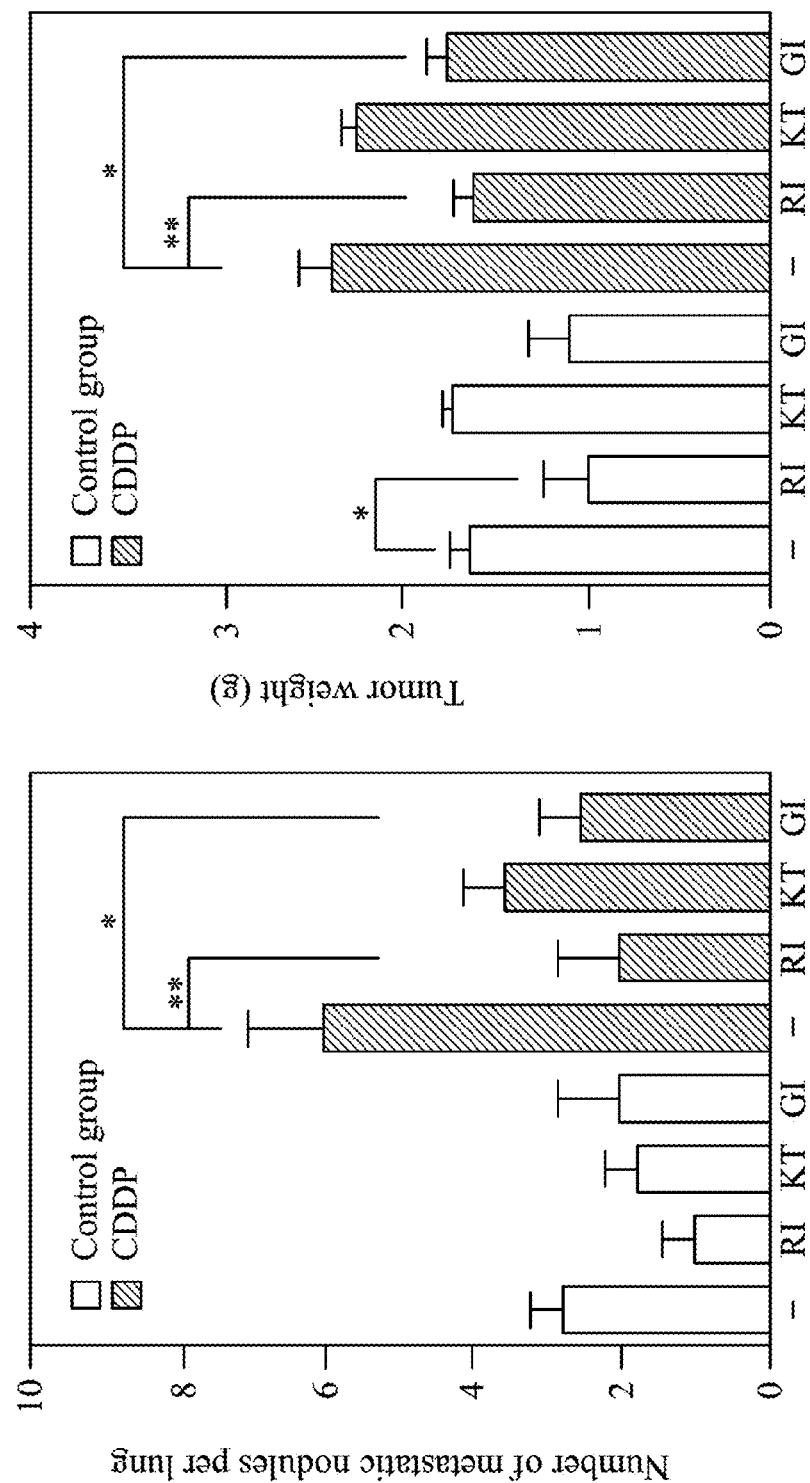
FIG. 4B shows bar diagrams of the number of metastatic nodules (left panel) and tumor weight (right panel) per lung of mice in FIG. 4A in vivo.

Reference was made to FIG. 4B, which showed bar diagrams of the number of metastatic nodules (left panel) and tumor weight (right panel) per lung of mice in FIG. 4A in vivo. According to the results shown in FIG. 4B, the short peptides RI37 and GI40 of Example 1 could inhibit tumor metastasis and growth, in which the short peptide RI37 had stronger inhibitory effect on the tumor growth, followed by the short peptide GI40, but the short peptide KT44 could not significantly inhibit tumor metastasis and growth.

Figure 4C:
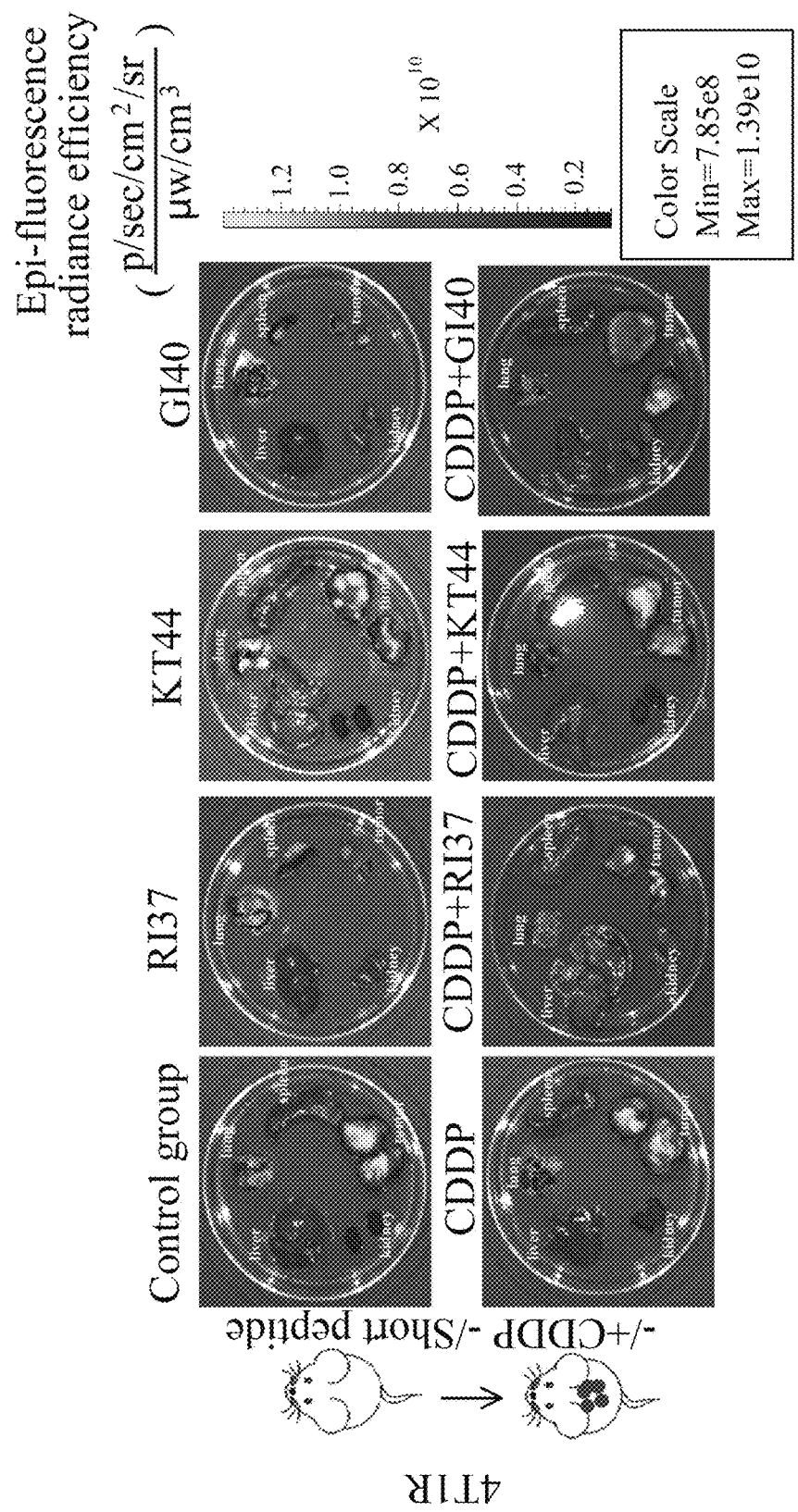
FIG. 4C shows images of the tumors of various organs of mice in FIG. 4A in vivo and epi-fluorescence radiance efficiency.

Reference was made to FIG. 4C, which showed images of the tumors of various organs of mice in FIG. 4A in vivo and epi-fluorescence radiance efficiency. According to the results shown in FIG. 4C, the short peptides RI37 and GI40 of Example 1 could inhibit tumor metastasis and growth, but the short peptide KT44 could not significantly inhibit tumor metastasis and growth, and metastatic nodules was found in lungs in the case of the short peptide KT44.

3. Evaluation of Influence of Xenograft Tumor Using Short Peptides

Figure 4D:
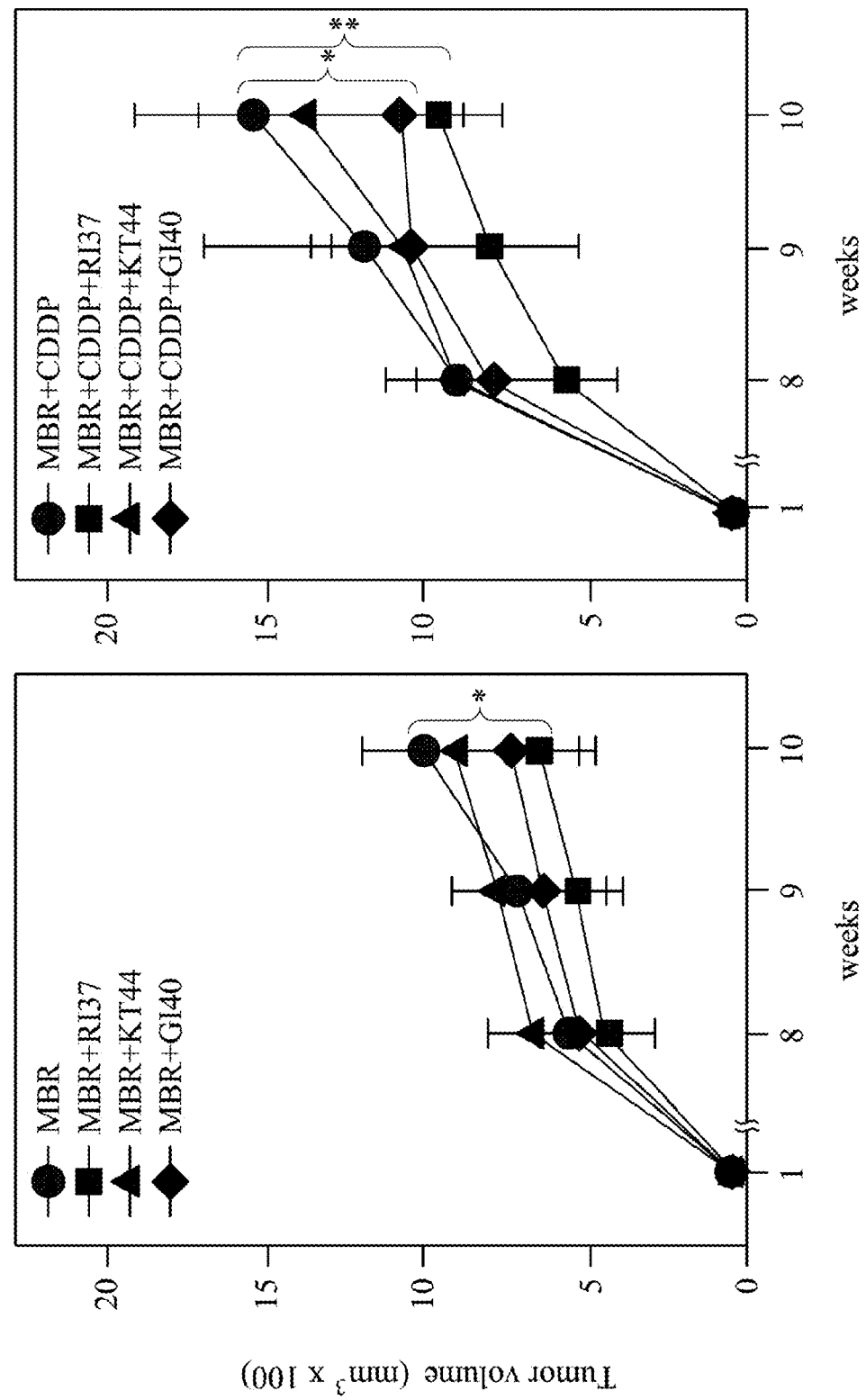
FIG. 4D shows curve diagrams of tumor size of drug-resistant MB231R breast cancer inhibited by several short peptides of Example 1 (left panel) or inhibited by combination with several short peptides of Example 1 and CDDP (right panel) in vivo.

Reference was made to FIG. 4D, which showed curve diagrams of tumor size of drug-resistant breast cancer MB231R cells inhibited by several short peptides of Example 1 (left panel) or inhibited by combination with several short peptides of Example 1 and CDDP (right panel) in vivo. According to the results shown in FIG. 4D, the short peptides RI37 and GI40 of Example 1 could inhibit tumor growth, reduce the drug resistance generated by the tumor from drug-resistant breast cancer MB231R cell, in which the short peptide RI37 had stronger inhibitory effect on the tumor growth, followed by the short peptide GI40, but the short peptide KT44 could not significantly inhibit the tumor growth.

Figure 4E:
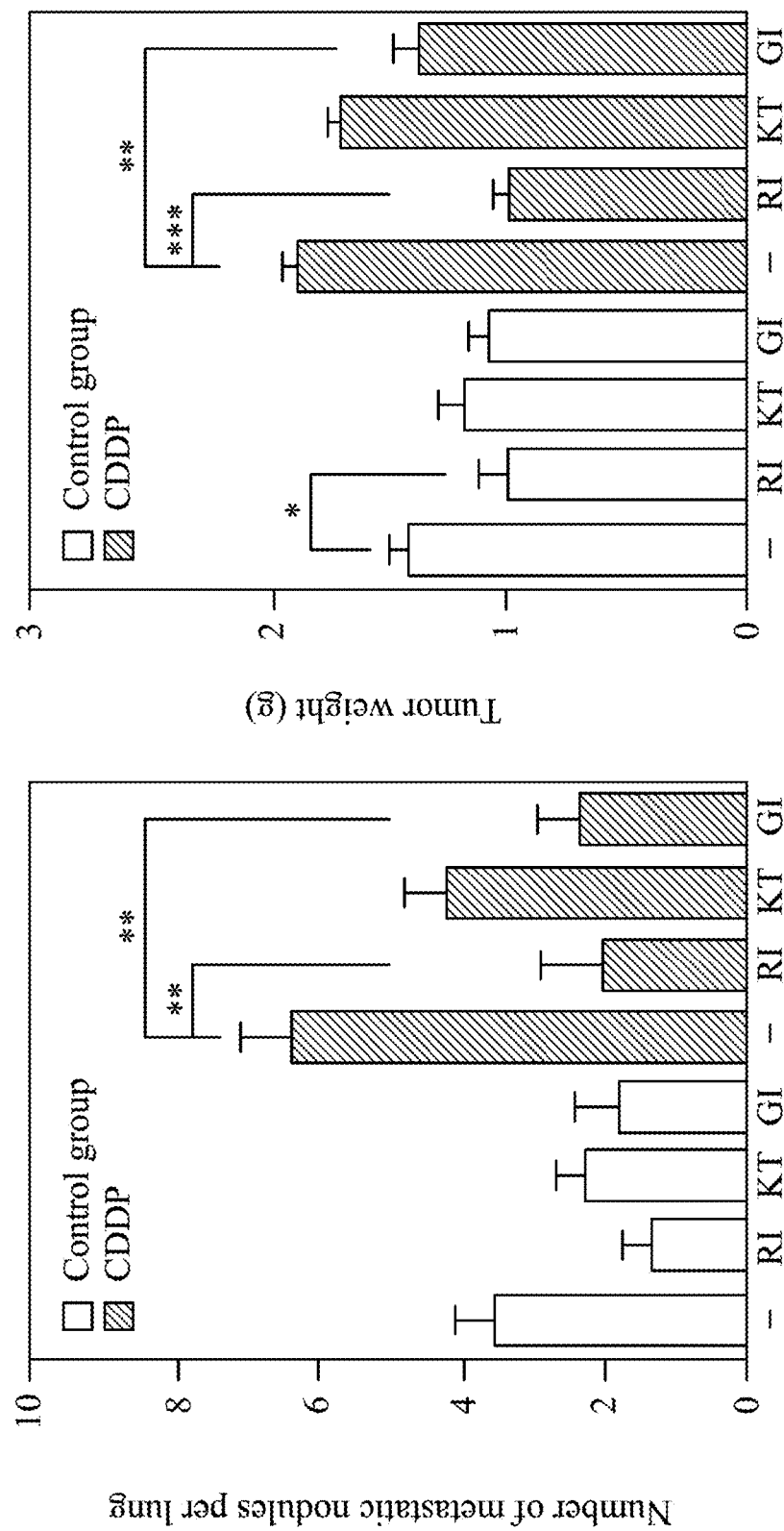
FIG. 4E shows bar diagrams of the number of metastatic nodules (left panel) and tumor weight (right panel) per lung of mice in FIG. 4D in vivo.

Reference was made to FIG. 4E, which showed bar diagrams of the number of metastatic nodules (left panel) and tumor weight (right panel) per lung of mice in FIG. 4D in vivo. According to the results shown in FIG. 4E, the short peptides RI37 and GI40 of Example 1 could inhibit tumor metastasis and growth, in which the short peptide RI37 had stronger inhibitory effect on the tumor growth, followed by the short peptide GI40, but the short peptide KT44 could not significantly inhibit tumor metastasis and growth.

Figure 4F:
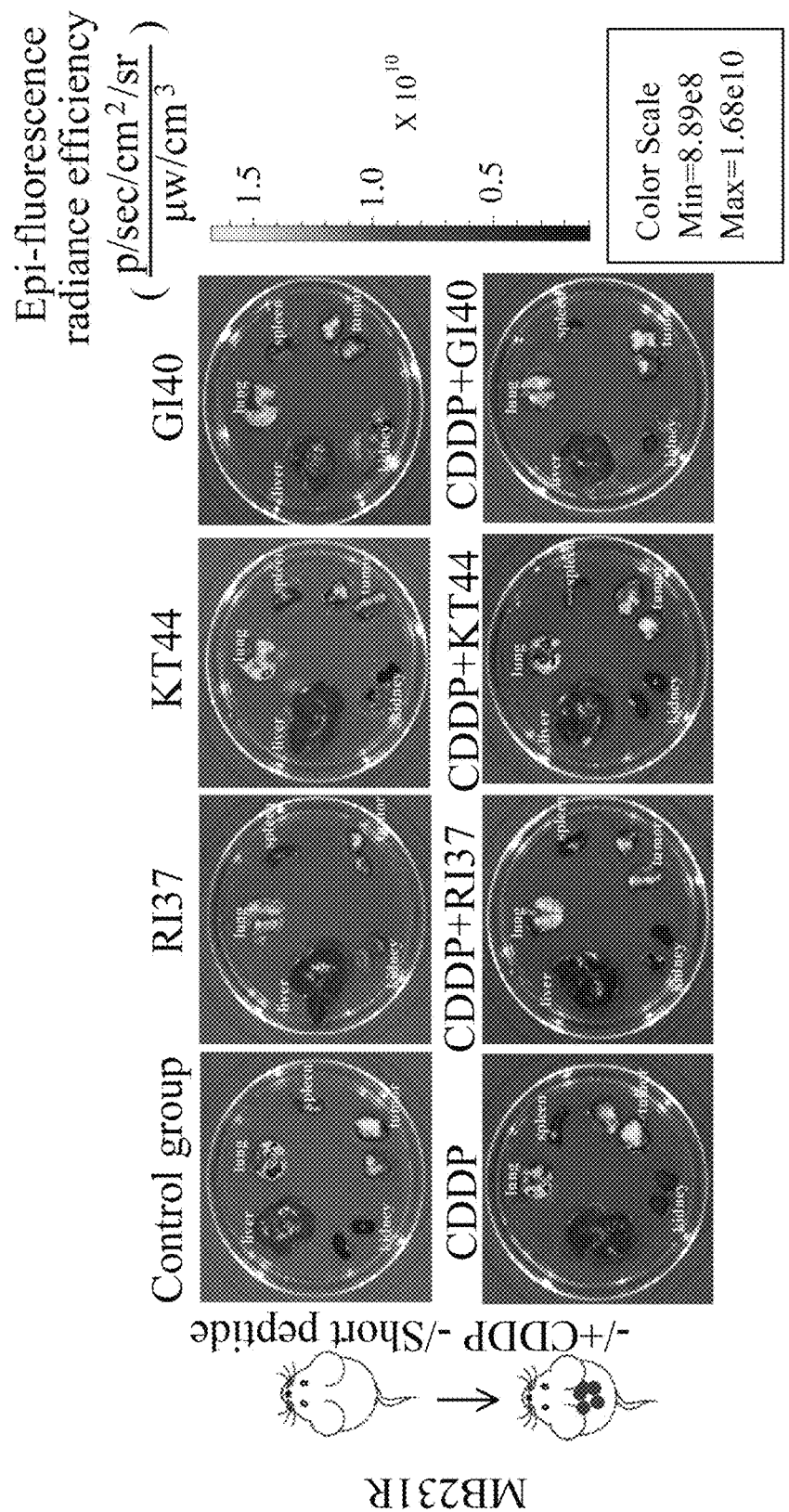
FIG. 4F shows images of the tumors of various organs of mice in FIG. 4D in vivo and epi-fluorescence radiance efficiency.

Reference was made to FIG. 4F, which showed images of the tumors of various organs of mice in FIG. 4D in vivo and epi-fluorescence radiance efficiency. According to the results shown in FIG. 4F, the short peptides RI37 and GI40 of Example 1 could inhibit tumor metastasis and growth, but the short peptide KT44 could not significantly inhibit tumor metastasis and growth, and metastatic nodules was found in lungs in the case of the short peptide KT44.

All data of those embodiments were obtained from triplet replications in each time point and each sample as mean plus or minus the averaged standard deviation. All data were analyzed in one way ANOVA. In the aforementioned embodiments, the symbol "*" was denoted to the data having static significance (p<0.05), the symbol "" was denoted to the data having static significance (p<0.01), and the symbol "*" was denoted to the data having static significance (p<0.001).

In summary, the aforementioned embodiments evidence that the short peptides RI37 and/or GI40 of Example 1 having no more than 40 amino acid residues can effectively inhibit the activity of endogenous PTX3, thereby specifically reducing or inhibiting activities of the cancer cells, for example, cancer cell proliferation, cancer stemness, cell migration, cancer cell invasion, metastasis or drug resistance. Therefore, the short peptides of Example 1 can serve as the short peptide-based therapeutic agent for applying to the preparation of the medicinal composition for specifically reducing or inhibiting the activity of PTX3.

It is necessarily supplemented that, specific short peptides, specific processes, specific analysis methods or specific apparatuses are exemplified for clarifying the short peptide-based therapeutic agent and medicinal composition including the same for inhibiting the activity of PTX3. However, as is understood by a person skilled in the art, other shorter peptides, other processes, other analysis methods or other apparatuses can be also adopted in the short peptide-based therapeutic agent and medicinal composition including the same of the present invention.

According to the embodiments of the present invention, the short peptide-based therapeutic agent and the medicinal composition including the same are beneficial to adapt the short peptides RI37 and/or GI40 having no more than 40 amino acid residues, which can effectively inhibit the activity of endogenous PTX3, thereby specifically reducing or inhibiting activities of the cancer cells, for example, cell cancer proliferation, cancer stemness, cell migration, cancer cell invasion, metastasis or drug resistance.

Although the present invention has been described in considerable detail with reference to certain embodiments thereof, other embodiments are possible. Therefore, the spirit and scope of the appended claims should not be limited to the description of the embodiments contained herein.

---

What is claimed is:

1. An unglycosylated peptide consisting of SEQ ID NO: 1, wherein the unglycosylated peptide specifically reduces or inhibits activities of cancer cells.

2. A medicinal composition comprising a therapeutic agent and a pharmaceutically acceptable carrier, wherein the therapeutic agent comprises an unglycosylated peptide consisting of SEQ ID NO: 1 as an active ingredient, and wherein the unglycosylated peptide specifically reduces or inhibits activities of cancer cells.

* * * * *